US011737883B2

United States Patent
Metcalfe et al.

(10) Patent No.: US 11,737,883 B2
(45) Date of Patent: Aug. 29, 2023

(54) ORTHOPAEDIC IMPLANTS INCLUDING BREAKAWAY FASTENER

(71) Applicant: Arthrex, Inc., Naples, FL (US)

(72) Inventors: Nick Metcalfe, Bonita Springs, FL (US); Steven Jim DeLeon, Naples, FL (US); Steven P. Schewe, Bradenton, FL (US); Timothy J. Thompson, Naples, FL (US); Kevin John Gallen, Naples, FL (US); Scott William Doody, Bonita Springs, FL (US); Michael Moreland, Fort Myers, FL (US)

(73) Assignee: ARTHREX, INC., Naples, FL (US)

( * ) Notice: Subject to any disclaimer, the term of this patent is extended or adjusted under 35 U.S.C. 154(b) by 149 days.

(21) Appl. No.: 17/189,465

(22) Filed: Mar. 2, 2021

(65) Prior Publication Data
US 2022/0280306 A1 Sep. 8, 2022

(51) Int. Cl.
*A61F 2/40* (2006.01)
*A61F 2/30* (2006.01)

(52) U.S. Cl.
CPC ............. *A61F 2/4081* (2013.01); *A61F 2/30* (2013.01); *A61F 2/40* (2013.01); *A61F 2002/30561* (2013.01); *A61F 2002/4085* (2013.01)

(58) Field of Classification Search
CPC .. A61F 2/30; A61F 2/40; A61F 2/4081; A61F 2002/30561; A61F 2002/4085; A61F 2002/30558
See application file for complete search history.

(56) References Cited

U.S. PATENT DOCUMENTS

| 6,231,611 | B1 | 5/2001 | Mosseri |
| 7,931,690 | B1 | 4/2011 | Bonutti |
| 7,993,408 | B2 * | 8/2011 | Meridew ............... A61F 2/4081 |
| | | | 623/22.32 |
| 8,303,665 | B2 | 11/2012 | Tornier et al. |
| 8,632,597 | B2 | 1/2014 | Lappin |

(Continued)

FOREIGN PATENT DOCUMENTS

| EP | 1273269 | 1/2003 |
| EP | 3415108 | 12/2018 |

(Continued)

OTHER PUBLICATIONS

International Search Report and Written Opinion for International Application No. PCT/US2022/016416 dated May 31, 2022.

(Continued)

*Primary Examiner* — Dinah Baria
(74) *Attorney, Agent, or Firm* — Carlson, Gaskey & Olds, P.C.

(57) ABSTRACT

This disclosure relates to orthopaedic implants and methods for restoring functionality to a joint. The implants described herein may be utilized during orthopaedic procedures and may be incorporated into a shoulder prosthesis for restoring functionality to shoulders having advanced cartilage disease. The disclosed implants may incorporate one or more fasteners formed together with a main body of the respective implant at a breakable connection. The fastener may be deployed during a surgical procedure, which may improve fixation of the implant at the surgical site.

27 Claims, 30 Drawing Sheets

(56) References Cited

U.S. PATENT DOCUMENTS

| | | |
|---|---|---|
| 8,852,283 B2 | 10/2014 | Tornier et al. |
| 8,940,054 B2 | 1/2015 | Wiley et al. |
| 9,114,017 B2 | 8/2015 | Lappin |
| 9,226,830 B2 | 1/2016 | De Wilde et al. |
| 9,233,003 B2 | 1/2016 | Rouche et al. |
| 9,283,083 B2 | 3/2016 | Winslow et al. |
| 9,452,055 B2 | 9/2016 | Lappin |
| 9,532,880 B2 | 1/2017 | Lappin |
| 9,545,312 B2 | 1/2017 | Tornier et al. |
| 9,629,725 B2 | 4/2017 | Gargac et al. |
| 9,844,440 B2 | 12/2017 | Kovacs et al. |
| 10,034,757 B2 | 7/2018 | Kovacs et al. |
| 10,265,184 B2 | 4/2019 | Lappin |
| 10,357,373 B2 | 7/2019 | Gargac et al. |
| 10,383,735 B2 | 8/2019 | Wiley et al. |
| 2015/0250594 A1* | 9/2015 | Ek .................. A61F 2/4606 623/23.4 |
| 2017/0095336 A1 | 4/2017 | Tornier et al. |
| 2018/0049897 A1 | 2/2018 | Lathers et al. |
| 2018/0161163 A1 | 6/2018 | Macke |
| 2018/0303618 A1 | 10/2018 | Kovacs et al. |
| 2018/0333268 A1 | 11/2018 | Cardon et al. |
| 2018/0338841 A1* | 11/2018 | Miller .................. A61F 2/4455 |
| 2018/0360512 A1 | 12/2018 | Mari |
| 2019/0015116 A1 | 1/2019 | Gargac et al. |
| 2019/0015117 A1 | 1/2019 | Neichel et al. |
| 2019/0015118 A1 | 1/2019 | Neichel et al. |
| 2019/0015221 A1 | 1/2019 | Neichel et al. |
| 2019/0151106 A1 | 5/2019 | Kovacs et al. |
| 2019/0159903 A1 | 5/2019 | Broghammer et al. |
| 2019/0159907 A1 | 5/2019 | Roche et al. |
| 2019/0240035 A1 | 8/2019 | Lappin |
| 2019/0298537 A1 | 10/2019 | Gargac et al. |

FOREIGN PATENT DOCUMENTS

| | | |
|---|---|---|
| EP | 3498227 | 6/2019 |
| WO | 2017007565 | 1/2017 |
| WO | 2017165346 | 9/2017 |
| WO | 2018052965 | 3/2018 |
| WO | 2018081073 | 5/2018 |
| WO | 2021021247 | 2/2021 |

OTHER PUBLICATIONS

Musculoskeletal Key. Arthrex Univers Revers (TM) shoulder prosthesis. Retrieve from: https://musculoskeletalkey.com/arthrex-univers-revers-shoulder-prosthesis/.

* cited by examiner

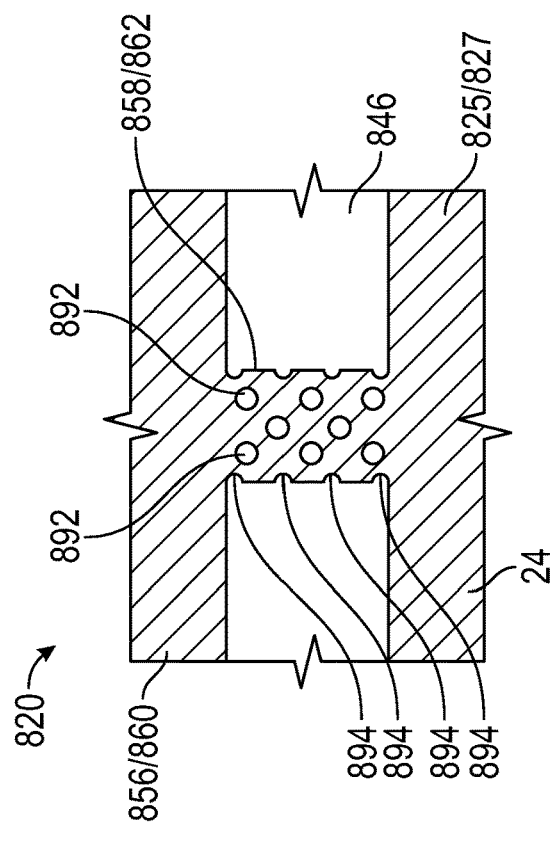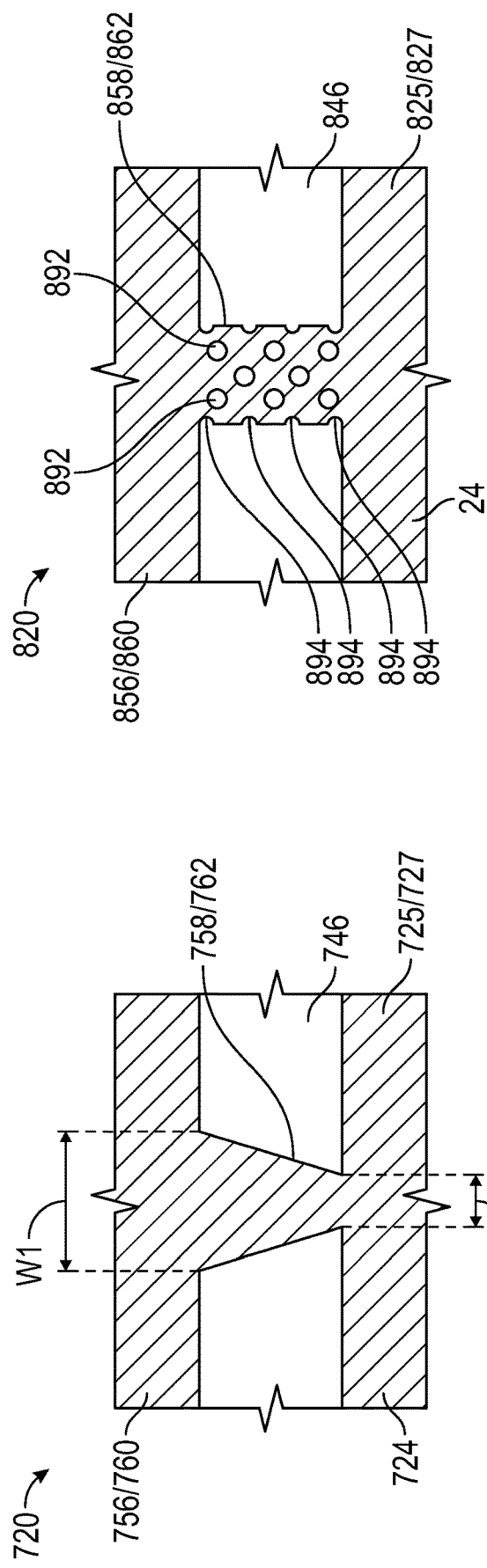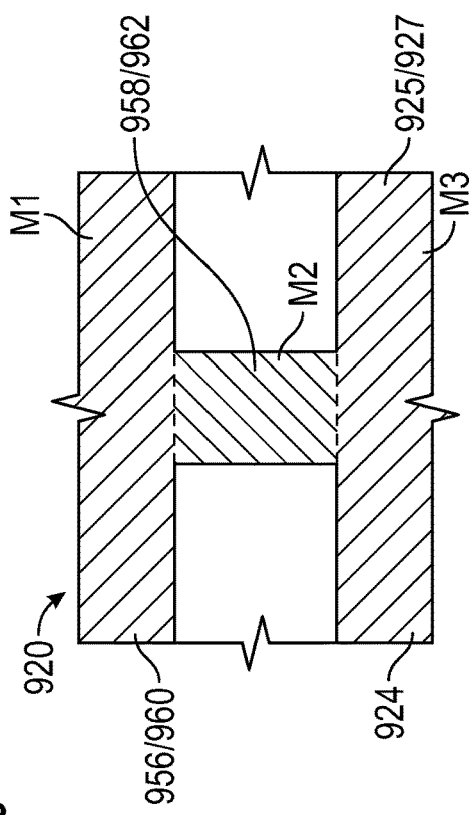
FIG. 33
FIG. 34
FIG. 35

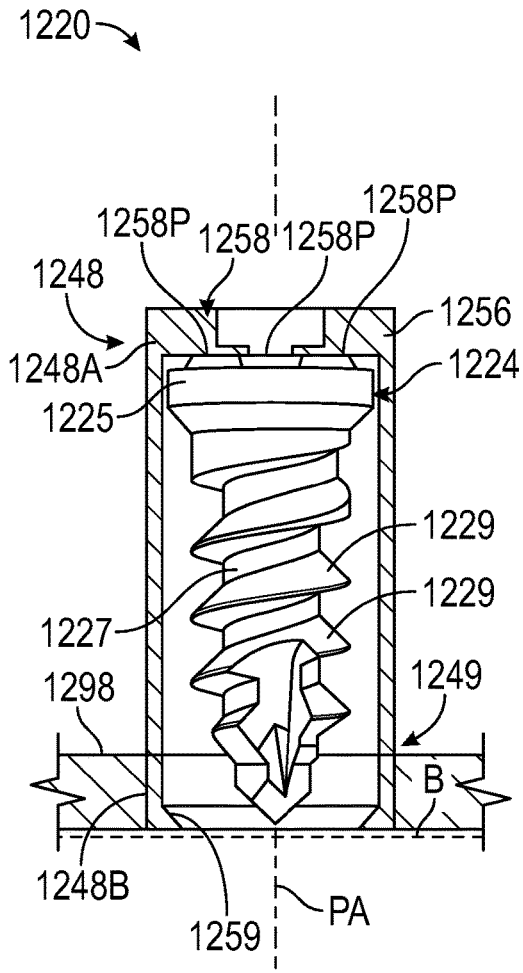 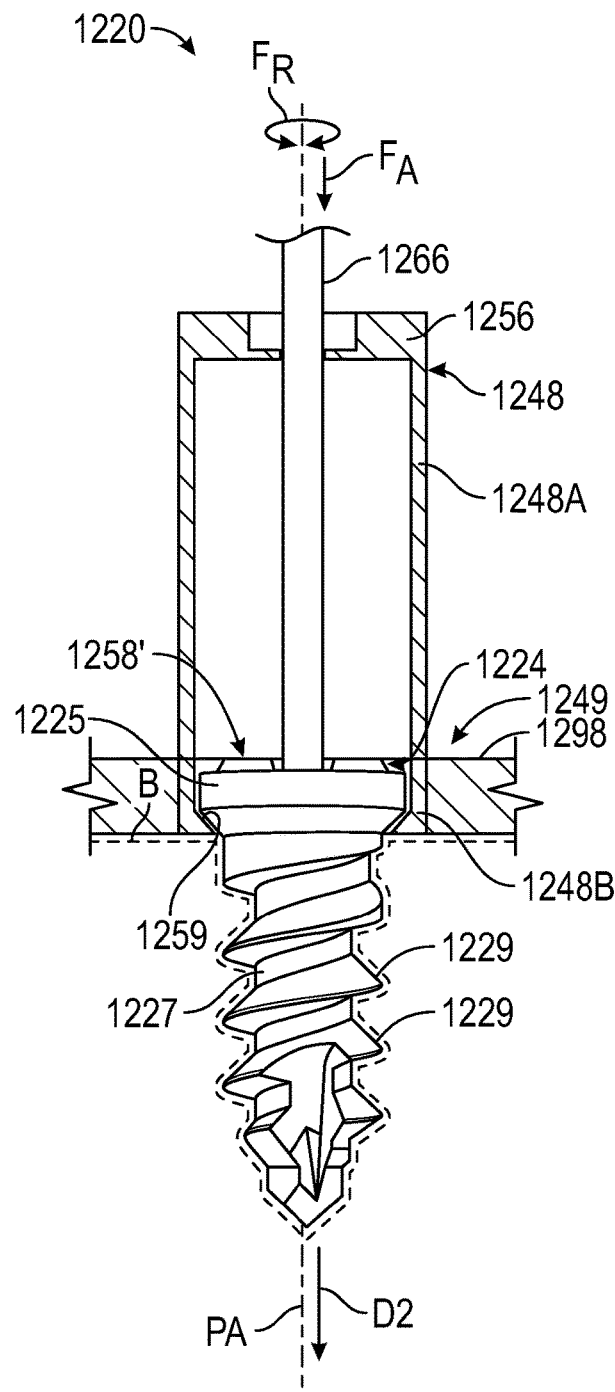
FIG. 42
FIG. 43

ORTHOPAEDIC IMPLANTS INCLUDING BREAKAWAY FASTENER

BACKGROUND

This disclosure relates to orthopaedic procedures and, more particularly, to orthopaedic implants and methods for restoring functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to fill a defect in the glenoid bone. The implant may be secured to the glenoid utilizing one or more fasteners.

SUMMARY

This disclosure relates to orthopaedic implants and methods. The implants may be used during methods for restoring functionality to a joint. The implant may include one or more fasteners coupled to a wall of the implant at a breakable connection.

An orthopaedic implant according to an exemplary aspect of this disclosure may include, inter alia, a main body including an inner wall establishing a passage. The passage may extend inwardly from an external surface of the main body. A fastener may be dimensioned to be partially received in bone. The fastener may be coupled to the internal wall at a first breakable connection along the passage. A portion of the fastener may be moveable outwardly from the passage in response to severing the first breakable connection.

A method of installing an orthopaedic implant at a surgical site according to an exemplary aspect of this disclosure may include, inter alia, positioning an implant along a bone at a surgical site. The implant may include a main body establishing a passage and a fastener coupled to an internal wall of the main body at a first breakable connection along the passage. The method may include engaging an interface of the implant with a driver. The method may include severing the first breakable connection in response to moving the driver at the interface, and then moving the driver to cause the fastener to move at least partially outwardly from the passage and into the bone to secure the implant at the surgical site.

A method of forming an orthopaedic implant according to an exemplary aspect of this disclosure may include, inter alia, printing a main body including an inner wall establishing a passage. The method may include printing a fastener at least partially in a volume of the passage. The fastener may be dimensioned to be at least partially received in bone. The method may include printing a first breakable connection that interconnects the internal wall of the main body and the fastener. A portion of the fastener may be moveable outwardly from the passage in response to severing the first breakable connection.

BRIEF DESCRIPTION OF THE DRAWINGS

FIGS. 33-37 illustrate exemplary breakable connections.

FIGS. 38-45 illustrate another exemplary orthopaedic implant in non-deployed and deployed states.

DETAILED DESCRIPTION

Figure 1:
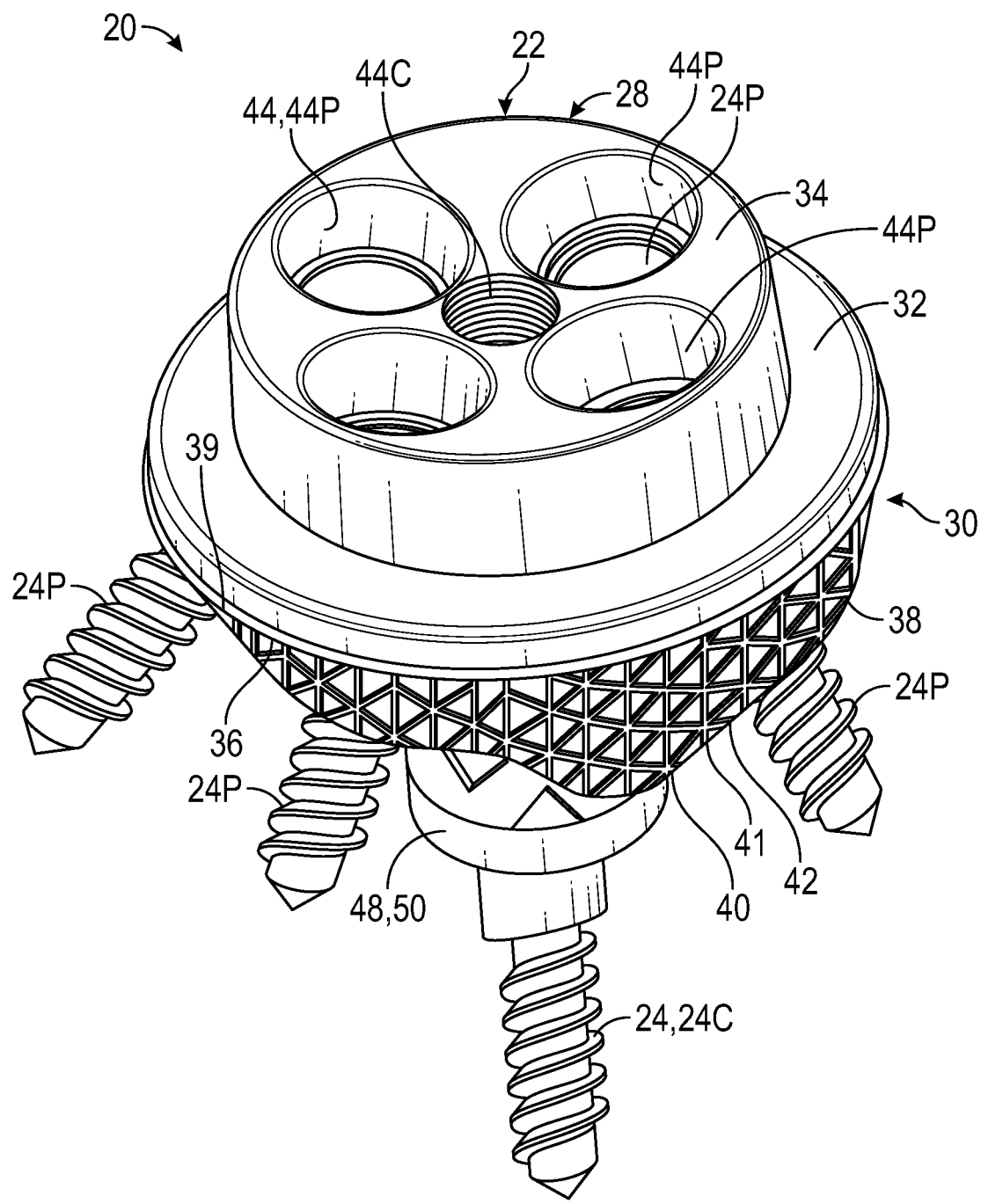
FIGS. 1-3 illustrate perspective and side views of an exemplary orthopaedic implant in a deployed state.

This disclosure relates to orthopaedic implants and methods of fabricating and installing implants. The implants described herein may be utilized during orthopaedic procedures and may be incorporated into a shoulder prosthesis for restoring functionality to shoulders having advanced cartilage disease. The disclosed implants may incorporate one or more fasteners that may be formed together with a main body of the respective implant. The fastener may be deployed during a surgical procedure according to a predetermined orientation and/or depth, which may reduce surgical duration and improve healing of the patient.

An orthopaedic implant according to an exemplary aspect of this disclosure may include, inter alia, a main body including an inner wall establishing a passage. The passage may extend inwardly from an external surface of the main body. A fastener may be dimensioned to be partially received in bone. The fastener may be coupled to the internal wall at a first breakable connection along the passage. A portion of the fastener may be moveable outwardly from the passage in response to severing the first breakable connection.

In a further embodiment, the fastener may be a compression screw including a plurality of threads.

In a further embodiment, the compression screw may include a head portion and a shank portion extending from the head portion. The plurality of threads may extend about a circumference of the shank portion. The fastener may be cantilevered in the passage from the first breakable connection at the head portion.

In a further embodiment, the main body may include a baseplate and an augment. The baseplate may include a plate body extending along a longitudinal axis between a front face and a rear face. The augment may include an augment body dimensioned to contact bone. The augment body may extend outwardly from the rear face of the baseplate to establish at least a portion of the passage.

In a further embodiment, the augment body may include a porous scaffold extending between the external surface of the implant and the internal wall.

In a further embodiment, the augment may include an anchoring stem that establishes the passage. The anchoring stem may be dimensioned to extend outwardly from the augment body.

In a further embodiment, the anchoring stem may include one or more bone growth openings circumferentially distributed about a periphery of the anchoring stem that interconnect the passage and an external surface of the anchoring stem.

In a further embodiment, the plate body may establish a central aperture extending along the longitudinal axis between the front face and the passage.

In a further embodiment, the plate body may establish a plurality of peripheral apertures circumferentially distributed about the central aperture relative to the longitudinal axis. The augment may establish a plurality of peripheral passages at least partially aligned with respective ones of the peripheral apertures along a passage axis. The peripheral passages may extend between the rear face of the baseplate and the external surface of the implant. Each respective pair of the peripheral apertures and the peripheral passages may be dimensioned to at least partially receive a respective fastener along the passage axis. Each respective fastener may be dimensioned to be at least partially received in bone.

In a further embodiment, an articulation member may be secured to the baseplate adjacent the front face. The articulation member may include an articulating surface dimensioned to mate with an opposed articular surface associated with an adjacent bone.

In a further embodiment, a driving member may be coupled to the fastener at a second breakable connection. The driving member may include an interface dimensioned to engage a driver to cause the first breakable connection to sever in response to a first predetermined quantity of torque at the interface. The second breakable connection may be dimensioned to sever in response to a second predetermined quantity of torque at the interface. The second predetermined quantity of torque may be greater than the first predetermined quantity of torque.

In a further embodiment, the second breakable connection may at least partially extend along the passage.

In a further embodiment, the first breakable connection may include a plurality of connection points extending between the fastener and the internal wall.

In a further embodiment, the fastener may establish a passage dimensioned to at least partially receive a guide wire.

A method of installing an orthopaedic implant at a surgical site according to an exemplary aspect of this disclosure may include, inter alia, positioning an implant along a bone at a surgical site. The implant may include a main body establishing a passage and a fastener coupled to an internal wall of the main body at a first breakable connection along the passage. The method may include engaging an interface of the implant with a driver. The method may include severing the first breakable connection in response to moving the driver at the interface, and then moving the driver to cause the fastener to move at least partially outwardly from the passage and into the bone to secure the implant at the surgical site.

In a further embodiment, the step of severing the first breakable connection may generate an audible click and/or tactile force.

In a further embodiment the implant may include a driving member coupled to the fastener at a second breakable connection. The driving member may establish the interface. The step of severing the first breakable connection may include causing the driver to apply a first torque at the interface that exceeds a first predetermined quantity of torque.

In a further embodiment, severing the second breakable connection may occur subsequent to the step of severing the first breakable connection in response to causing the driver to apply a second torque at the interface that may exceed a second predetermined quantity of torque.

In a further embodiment, the main body may include an anchoring stem that establishes at least a portion of the passage. A portion of the anchoring stem may establish a plurality of bone growth openings circumferentially distributed about a periphery of the anchoring stem that interconnect the passage and an external surface of the anchoring stem. The method may include forming a recess in the bone. The method may include positioning the portion of the anchoring stem in the recess.

In a further embodiment, the passage may extend along a longitudinal axis. The main body may establish a plurality of peripheral apertures circumferentially distributed about the longitudinal axis. The method may include positioning a plurality of fasteners at least partially in respective ones of the peripheral apertures and then at least partially into the bone to secure the implant at the surgical site.

In a further embodiment, the method may include securing an articulation member to a front face of the main body. The articulation member may include an articulating surface dimensioned to mate with an opposed articular member associated with an adjacent bone at the surgical site.

A method of forming an orthopaedic implant according to an exemplary aspect of this disclosure may include, inter alia, printing a main body including an inner wall establishing a passage. The method may include printing a fastener at least partially in a volume of the passage. The fastener may be dimensioned to be at least partially received in bone. The method may include printing a first breakable connection that interconnects the internal wall of the main body and the fastener. A portion of the fastener may be moveable outwardly from the passage in response to severing the first breakable connection.

In a further embodiment, the step of printing the fastener may include printing a head portion, a shank portion extending from the head portion, and a plurality of threads about a circumference of the shank portion.

In a further embodiment, the step of printing the fastener may occur such that the fastener is cantilevered in the passage from the first breakable connection at the head portion.

In a further embodiment, the method may include printing a driving member including an interface. The method may include printing a second breakable connection interconnecting the driving member and the head portion of the fastener. The interface may be dimensioned to engage a driver to cause the first breakable connection to sever in response to a first predetermined quantity of torque at the interface. The second breakable connection may be dimensioned to sever in response to a second predetermined quantity of torque at the interface. The second predetermined quantity of torque may be greater than the first predetermined quantity of torque.

In a further embodiment, at least a portion of the second breakable connection may be established along the passage.

In a further embodiment, the step of printing the main body may include printing an augment including an augment body onto a rear face of a baseplate. The augment body may be dimensioned to contact bone. The baseplate may include a plate body extending between a front face and the rear face.

In a further embodiment, the plate body may establish a central aperture extending along a longitudinal axis between the front face and the passage. The plate body may establish a plurality of peripheral apertures circumferentially distributed about the longitudinal axis. The step of printing the augment may include establishing a plurality of peripheral passages at least partially aligned with respective ones of the peripheral apertures along a passage axis. Each of the peripheral passages may extend between the rear face of the baseplate and an external surface of the augment. Each respective pair of the peripheral apertures and the peripheral passages may be dimensioned to at least partially receive a respective fastener along the passage axis. Each respective fastener may be dimensioned to be partially received in bone.

In a further embodiment, the augment body may include a porous scaffold that establishes the external surface of the augment.

In a further embodiment, the step of printing the main body may include printing an anchoring stem to establish the inner wall. The scaffold may at least partially surround the anchoring stem.

In a further embodiment, the step of printing the anchoring stem may include establishing an array of bone growth openings circumferentially distributed about a periphery of the anchoring stem that interconnect the passage and an external surface of the anchoring stem. The anchoring stem may be dimensioned to extend outwardly from the augment body along the longitudinal axis.

FIGS. 1-9 illustrate an exemplary orthopaedic implant 20. The implant 20 may be utilized for various surgical procedures, such as an arthroplasty for restoring functionality to a joint. The implant 20 may be incorporated into a shoulder prosthesis for implantation in a glenoid, for example. Although the implants disclosed herein primarily refer to repair of a defect in a glenoid during a shoulder reconstruction, such as an anatomical and/or reverse shoulder procedure, it should be understood that the disclosed implants may be utilized in other locations of the patient and other surgical procedures.

Figure 2:
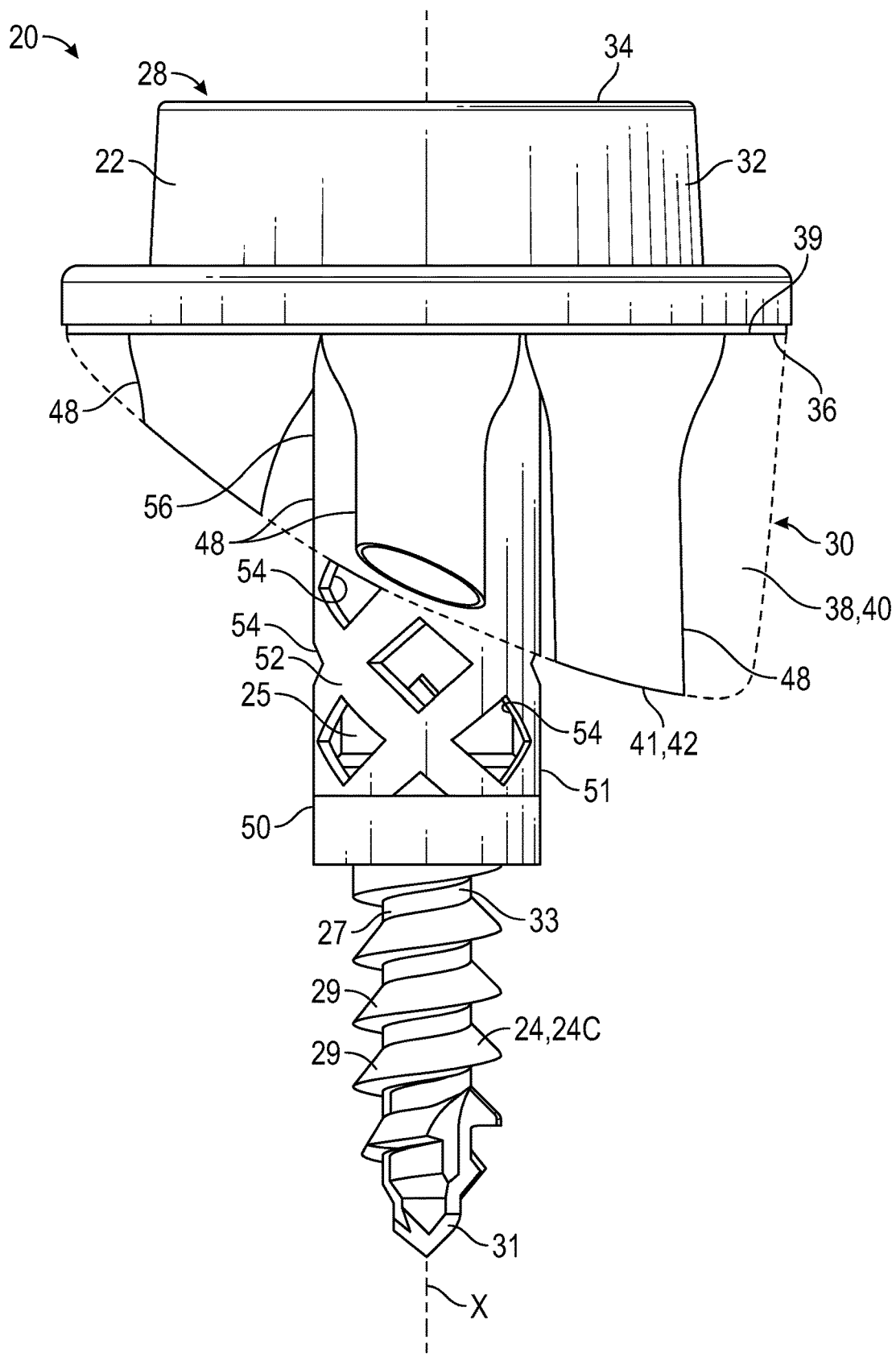
Figure 6:
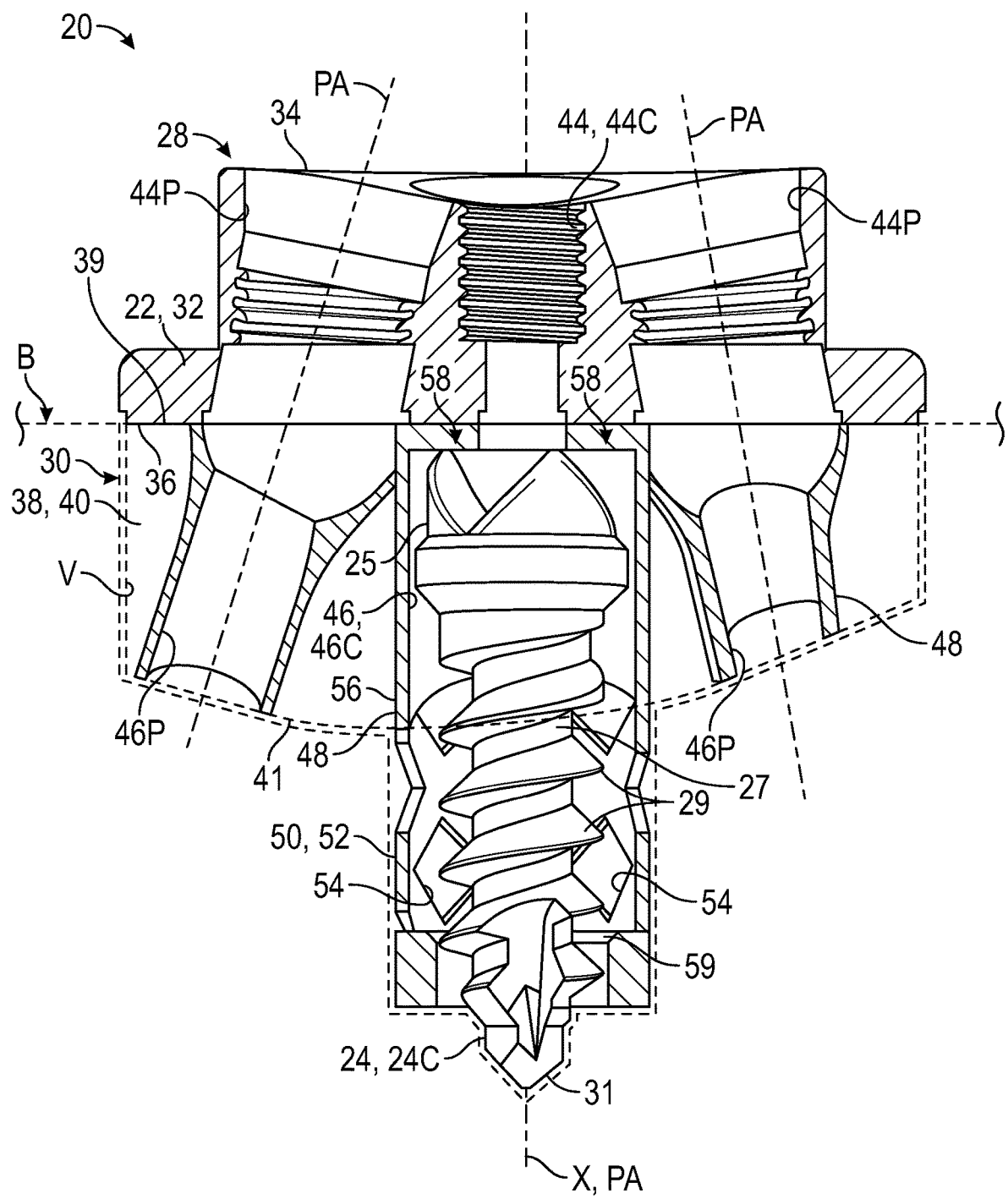
FIGS. 6-8 illustrates sectional views of the implant in the non-deployed state.

Referring to FIG. 1, the implant 20 may include a main body 22 dimensioned to abut against bone at a surgical site. The main body 22 may be dimensioned to receive one or more fasteners 24. Each of the fasteners 24 may be dimensioned to be at least partially received in bone to secure the implant 20 at the surgical site. One or more of the fasteners 24 may be removeable from the main body 22. Various fasteners 24 may be utilized with the implant 20, such as nails and compression screws. For example, each of the fasteners 24 may be a compression screw including a head portion 25 and a shank portion 27 extending outwardly from the head portion 25 to a respective tip portion 31, as illustrated in FIGS. 2 and 6. A plurality of threads 29 may extend about a circumference 33 of the shank portion 27 to engage tissue such as bone, as illustrated by FIG. 2.

The main body 22 may include a baseplate 28 and an augment 30. The augment 30 is shown in dashed lines in FIGS. 2 and 6 and is omitted in FIGS. 3, 5 and 7 for illustrative purposes. The baseplate 28 and augment 30 may be integrally formed to establish a monolithic or unitary component or may be separate and distinct components that are fixedly attached or otherwise secured to one another. The baseplate 28 may include a plate body 32 extending along a longitudinal axis X (FIG. 2) between a first (e.g., front) face 34 and a second (e.g., rear) face 36 generally opposed to the first face 34. A perimeter of the plate body 32 may have a substantially circular or elliptical geometry. A substantially circular geometry may reduce a reaming width and complexity of preparing a surgical site to accept the implant 20.

The augment 30 may include an augment body 38 dimensioned to contact bone. The augment body 38 may be formed according to a geometry that substantially matches a geometry of the bone of the respective patient. The augment body 38 may extend along the longitudinal axis X (FIG. 2) between a first (e.g., front) face 39 and a second (e.g., rear) face 41 generally opposed to the first face 39. The front faces 34, 39 may generally correspond to a lateral side of a patient, and the rear faces 36, 41 may generally correspond to a medial side of the patient when implanted in a surgical site. The augment body 38 may extend outwardly from the rear face 36 of the baseplate 28 to establish an external surface 42 of the implant 20.

The augment body 38 may be dimensioned to approximate various defect geometries and surface contours that may be encountered along a surgical site. The augment body 38 may be configured to at least partially or completely fill a recess or void V in a bone B such as a glenoid, as illustrated in dashed lines in FIG. 6.

Figure 4:
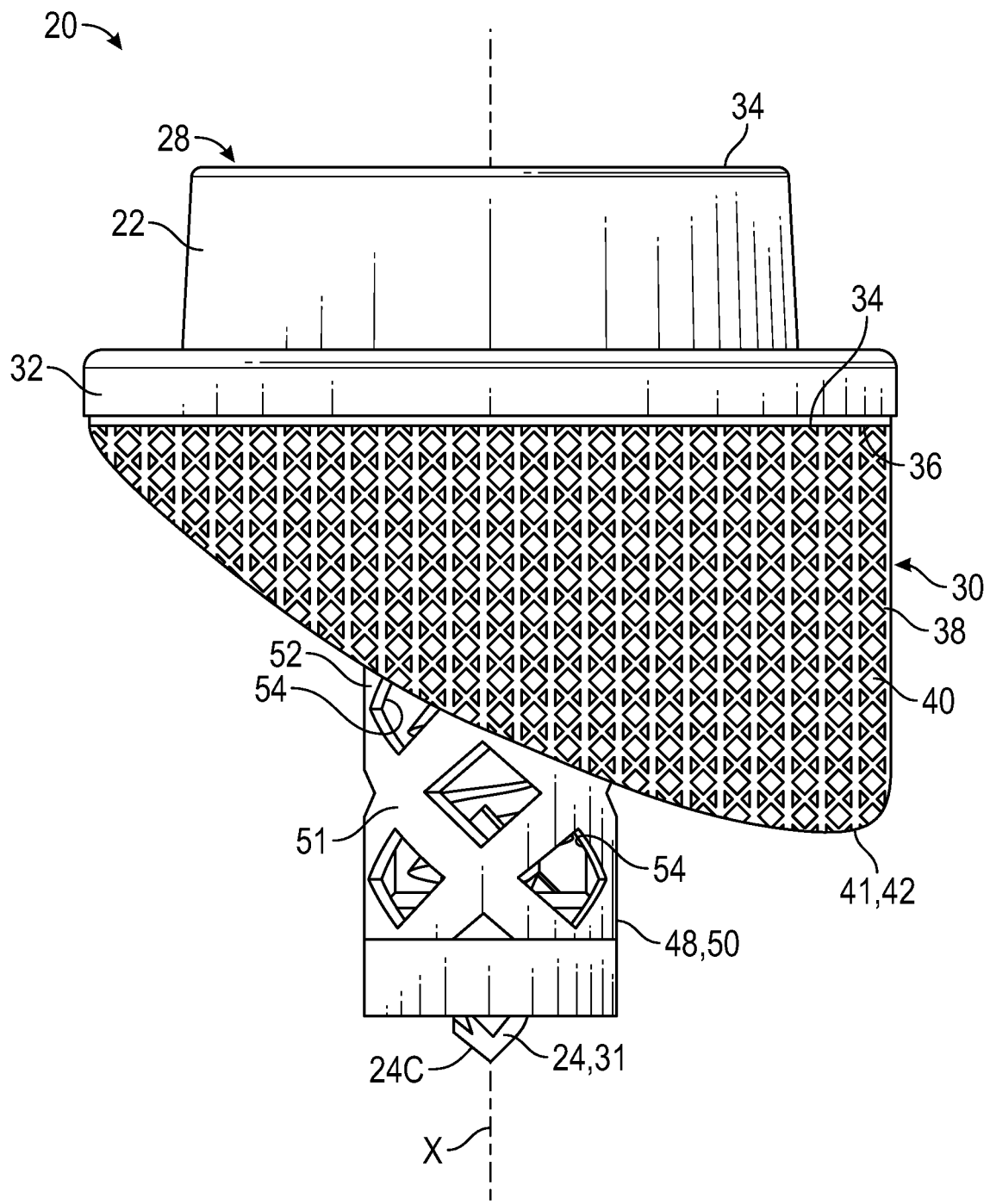
FIGS. 4-5 illustrate the implant in a non-deployed state.

The augment body 38 may include a porous scaffold 40 extending between the rear face 36 of the baseplate 28 and the external surface 42 of the implant 20 established by the rear face 41 of the augment body 38, as illustrated in FIG. 1 (see also FIG. 4). The scaffold 40 may include an interconnected network of branches and nodes extending throughout a volume of the augment body 38. The scaffold 40 may be infused with biological material or biologics to improve healing. The scaffold 40 is omitted from FIGS. 2, 5 and 7-8 for illustrative purposes. In other implementations, the augment body 38 may be substantially solid.

The plate body 32 of the baseplate 28 or another portion of the main body 22 may establish one or more apertures 44 dimensioned to receive a respective fastener, such as one of the fasteners 24. Each aperture 44 may extend along a respective passage axis PA between the front face 34 and the rear face 36 of the baseplate 28. The apertures 44 may include a central aperture 44C and one or more peripheral apertures 44P. The passage axis PA of the central aperture 44C may be substantially colinear with or otherwise parallel to the longitudinal axis X. The peripheral apertures 44P may be circumferentially distributed about the central aperture 44C relative to the longitudinal axis X, as illustrated by FIGS. 1 and 6-7.

Figure 7:
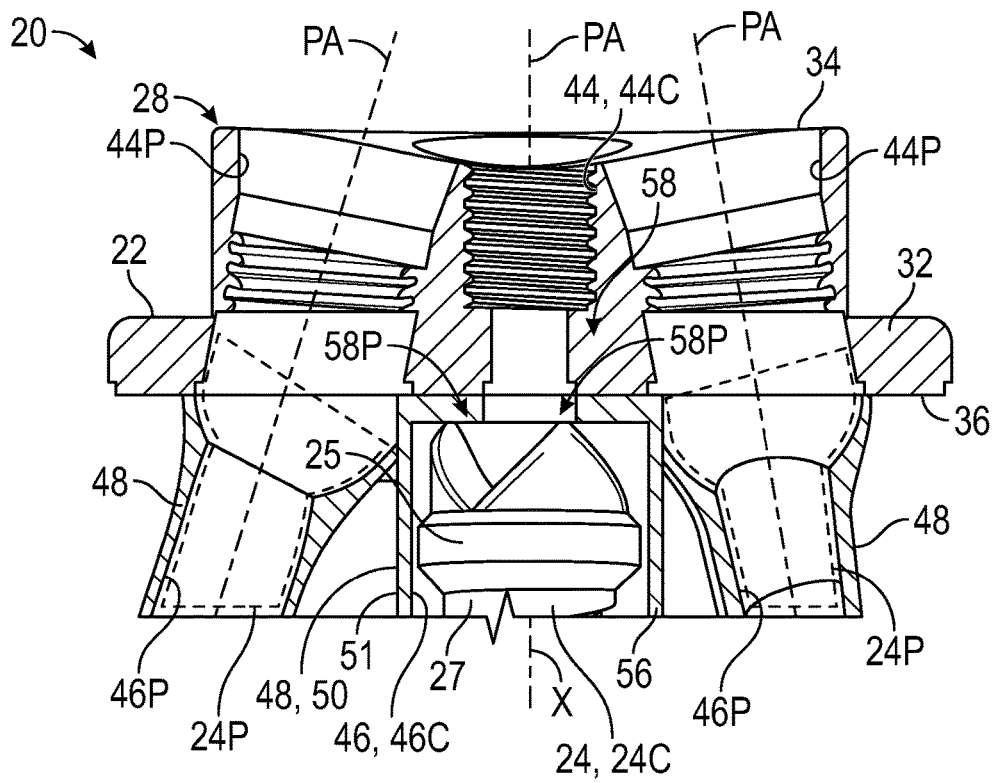

Referring to FIGS. 6-7, with continuing reference to FIG. 1, an inner wall 56 of the main body 22 such as the augment 30 may be dimensioned to establish one or more passages 46. The augment body 38 may extend outwardly from the rear face 36 of the baseplate 28 to establish at least a portion of each of the passages 46. Each passage 46 may extend inwardly from the external surface 42 of the main body 22. Each of the passages 46 may be dimensioned to receive a respective one of the fasteners 24. The passages 46 may extend between the front face 39 and rear face 41 of the augment 30, as illustrated in FIG. 6.

The passages 46 may include a central passage 46C and one or more peripheral passages 46P extending at least partially through the augment 30. The central passage 46C may be at least partially aligned with the central aperture 44C along the respective passage axis PA. The central passage 46C may extend along the longitudinal axis X. The peripheral passages 46P may be at least partially aligned with respective ones of the peripheral apertures 44P along the respective passage axes PA.

Each aperture 44 may extend along the respective passage axis PA between the front face 34 of the baseplate 28 and a respective one of the passages 46. The central aperture 44C may extend along the longitudinal axis X between the front face 34 of the baseplate 28 and the central passage 46C, as illustrated in FIGS. 6-7.

The fasteners 24 may include a central fastener 24C and one or more peripheral fasteners 24P (see FIG. 1). Each respective pair of the peripheral apertures 44P and peripheral passages 46P may be dimensioned to at least partially receive a respective peripheral fastener 24P along the passage axis PA (fasteners 24P indicated in dashed lines in FIG. 7 for illustrative purposes). The central passage 46C may be dimensioned to at least partially receive the central fastener 24C along the respective passage axis PA. The central fastener 24C may be spaced apart from the central aperture 44C.

The augment 30 may include one or more tubular members 48 extending between the rear face 36 of the baseplate 28 and the external surface 42 of the implant 20 established by the rear face 41 of the augment 30. Each tubular member 48 may establish a respective one of the passages 46. The scaffold 40 may extend between the external surface 42 of the implant 20 and the internal wall 56, as illustrated in FIGS. 2 and 6. The scaffold 40 may substantially surround the passages 46 and tubular members 48 within the augment body 38.

At least one of the tubular members 48 may serve as an anchoring stem 50 dimensioned to extend outwardly from the external surface 42 of the implant 20. The anchoring stem 50 may be dimensioned to extend along the longitudinal axis X to establish the central passage 46C, as illustrated in FIG. 6. In some implementations, one or more of the tubular members 48 extending from the peripheral apertures 44P may be dimensioned to extend outwardly from the external surface 42 to establish a respective anchoring stem. The anchoring stem 50 may be dimensioned to extend outwardly from the rear face 41 of the augment 30, as illustrated by FIG. 6, or another portion of the augment 30 that establishes the external surface 42 of the implant 20.

A periphery 51 of the anchoring stem 50 may be substantially solid (see, e.g., FIG. 10) or may be fenestrated to establish one or more openings for facilitating flow of blood, nutrients and other biological matter into and through the respective passage 46. For example, the anchoring stem 50 may include a cage 52 establishing one or more bone growth openings 54, as illustrated in FIG. 6. The openings 54 may be dimensioned to promote bone ingrowth, which may improve fixation of the implant 20 to an adjacent bone. The bone growth openings 54 may be circumferentially distributed about the periphery 51 of the anchoring stem 50 such that the openings 54 interconnect the respective passage 46 and an external surface of the anchoring stem 50.

Figure 3:
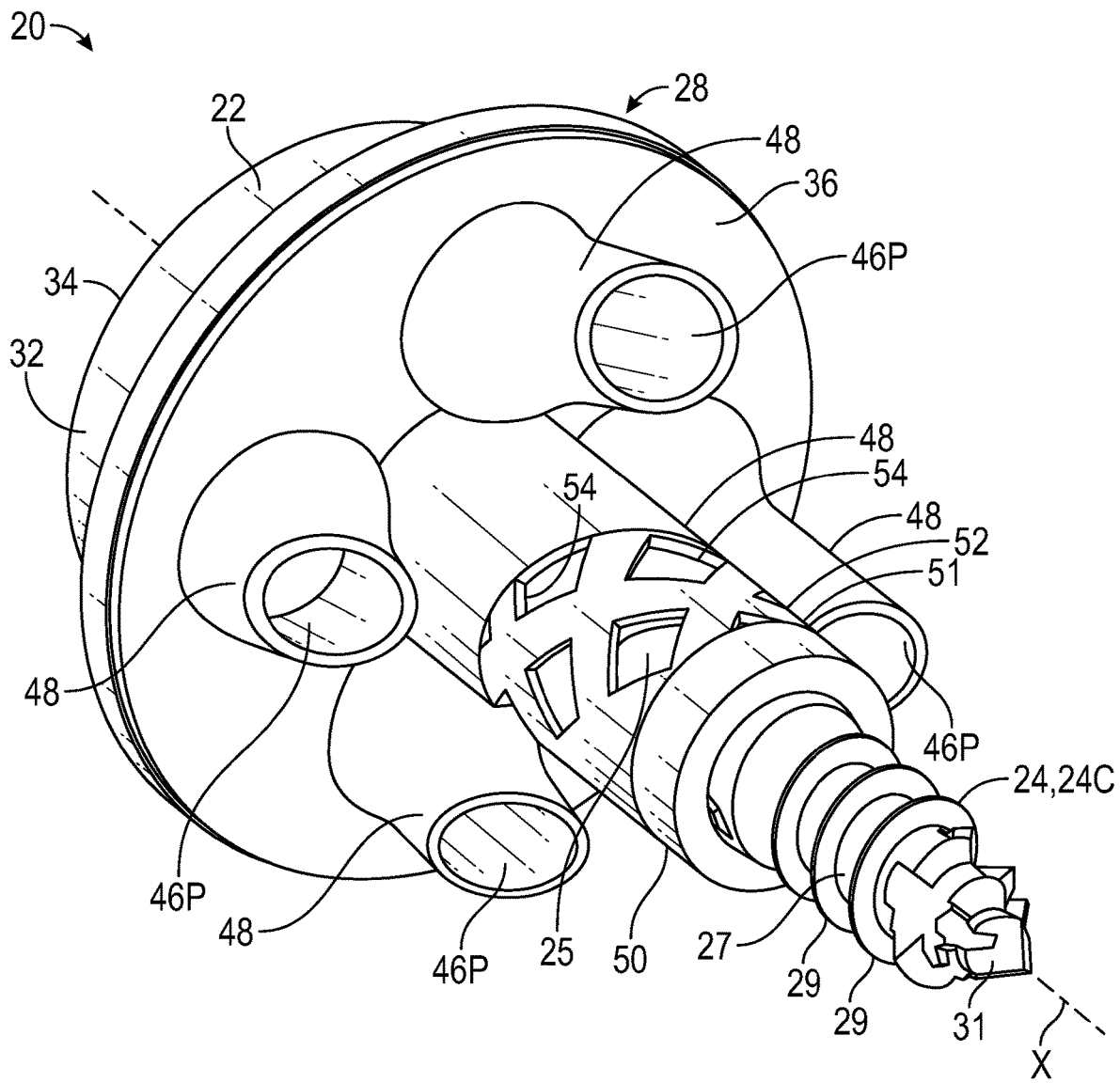
Figure 5:
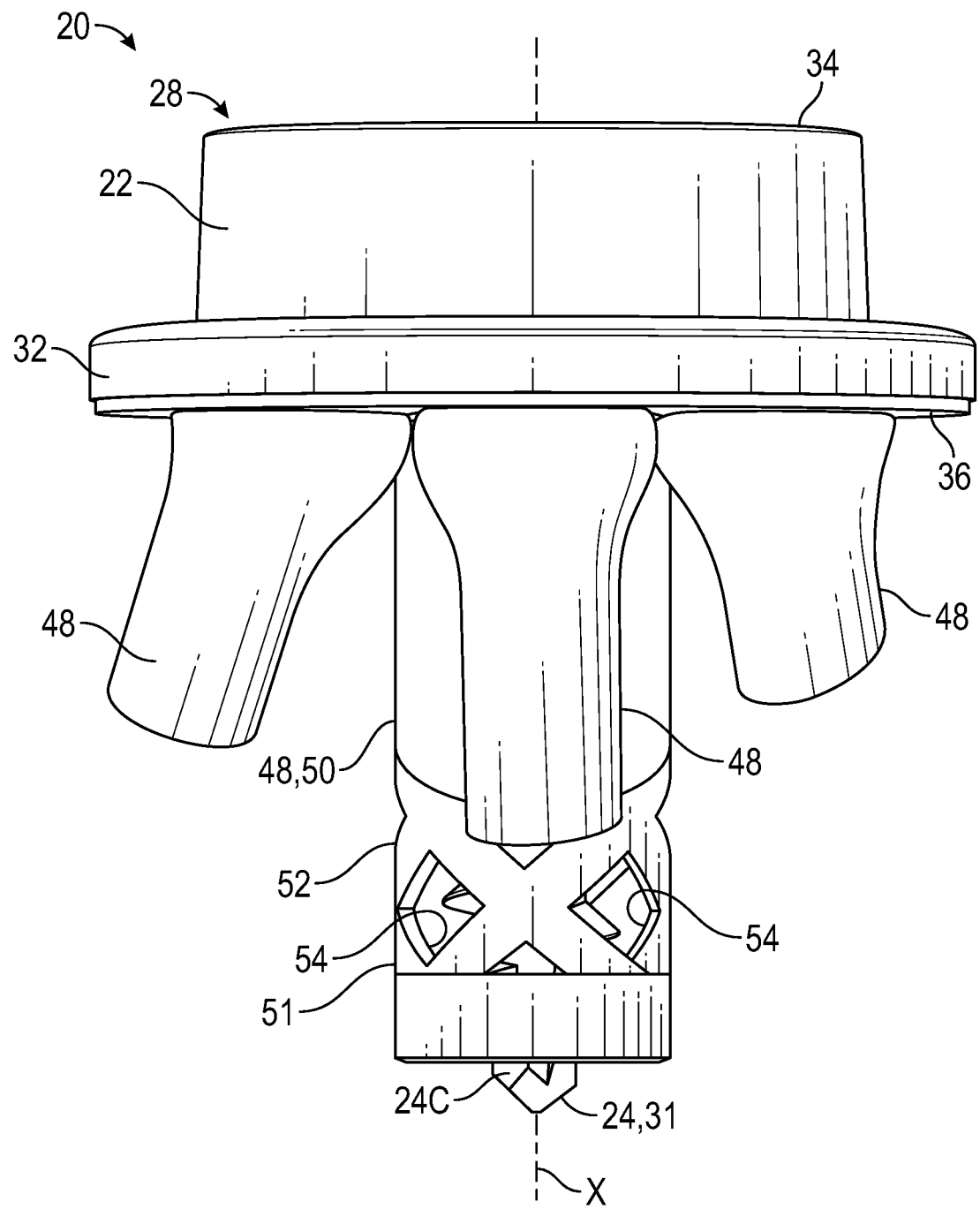

The surgeon may deploy the central fastener 24C to secure the implant 20 at the surgical site. FIGS. 1-3 illustrate the central fastener 24C in a deployed state. FIGS. 4-6 illustrate the central fastener 24C in non-deployed (e.g., initial) state. The non-deployed state may correspond to a fabricated state of the implant 20 prior to a surgical procedure. The central fastener 24C may be movable between the non-deployed and deployed states such that deployment of the central fastener 24C causes a permanent change to the implant 20.

Figure 8:
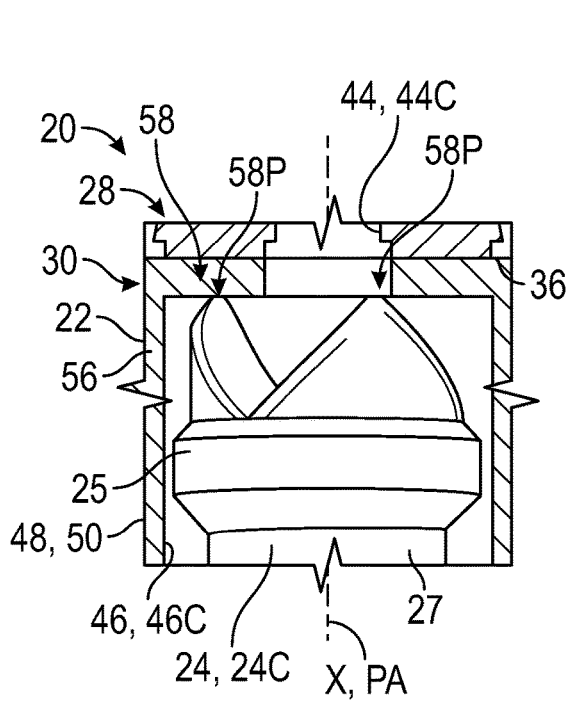
Figure 9:
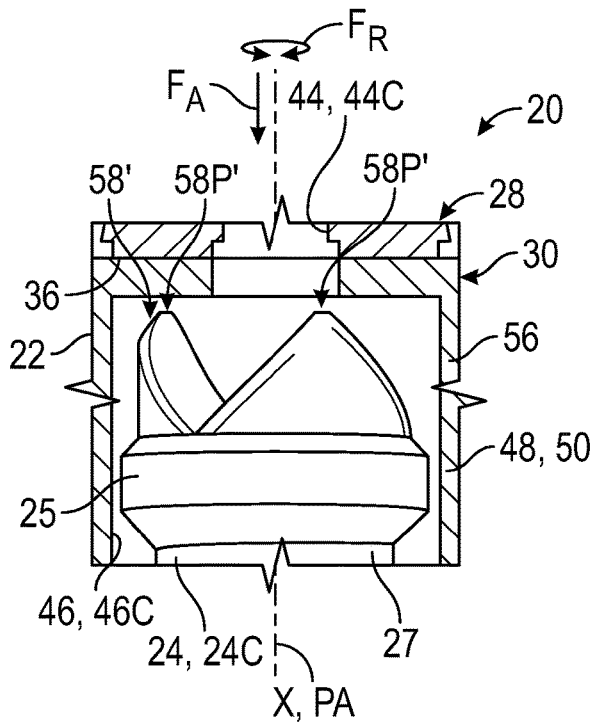
FIG. 9 illustrates a sectional view of the implant in the deployed state.

Referring to FIGS. 7-8, with continuing reference to FIG. 6, one or more of the fasteners 24, such as the central fastener 24C, may be coupled to the internal wall 56 at a first breakable (e.g., breakaway) connection 58 along the respective passage 46. The first breakable connection 58 may include one or more separate and discreet breakable connection points 58P distributed along surfaces of the inner wall 56 and head portion 25 of the fastener 24. Each of the breakable connection points 58P may be a frangible connection having a reduced thickness, scoring, perforations, and/or different material compositions (e.g., different densities), etc., to facilitate severing the fastener 24 from the inner wall 56 of the implant 20. In some implementations, the first breakable connection 58 is a single breakable connection point 58P. The first breakable connection 58 may interconnect the fastener 24 and inner wall 56 such that the fastener 24 is integrally formed with the main body 22, as illustrated in FIGS. 7-8.

The fastener 24 may be cantilevered or suspended in the passage 46 from the first breakable connection 58 at the head portion 25, as illustrated in FIG. 6. The cantilevered arrangement of the fastener 24 may be established such that the shank portion 27 substantially floats within the passage 46 in the non-deployed state. The implant 20 may be formed such that the first breakable connection 58 serves as the only point of connection and contact between the fastener 24 and the inner wall 56 in the non-deployed state. In some implementations, other portions of the fastener 24 may be dimensioned to contact surfaces of the inner wall 56 in the non-deployed state. Portions of the fastener 24, including the head portion 25 and/or threads 29, may contact the inner wall 56 during deployment of the fastener 24.

The first breakable connection 58 may be dimensioned to be severed in response to a predetermined amount of force applied to the head portion 25 or another portion of the fastener 24. For example, the first breakable connection 58 may be severed by applying an axial force $F_A$ and/or rotational force $F_R$ relative to the passage axis PA, as illustrated by first breakable connection 58' of FIG. 9. The first breakable connection 58 may be dimensioned to sever in response to a first predetermined quantity of torque applied to the fastener 24, such as applying the force $F_R$ about the passage axis PA.

Severing the first breakable connection 58 permanently causes the fastener 24 to move from the non-deployed state to the deployed state. A portion of the fastener 24 may be movable outwardly from the passage 46 in response or otherwise subsequent to severing the first breakable connection 58, as illustrated in FIGS. 2-3. The head portion 25 of the fastener 24 may be dimensioned to contact an abutment 59 to limit movement of the fastener 24 along the passage axis PA, as illustrated by implant 320 of FIG. 19 (see also FIG. 6).

Figure 10:
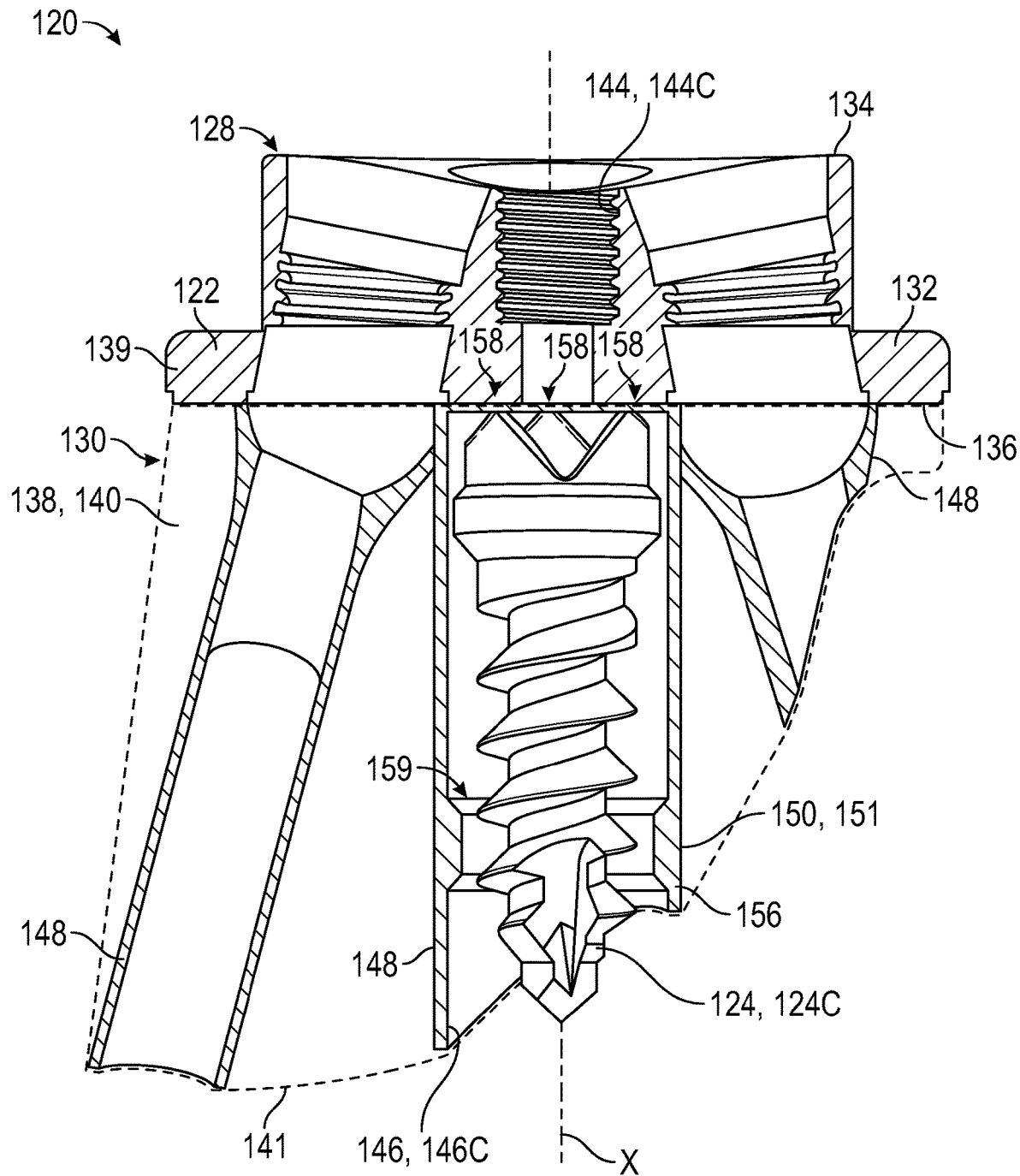
FIG. 10 illustrates another exemplary orthopaedic implant.

FIG. 10 illustrates another exemplary orthopedic implant 120. The implant 120 may include a main body 122 including a baseplate 128 and augment 130. The augment 130 may include a scaffold 140 and one or tubular members 148 (scaffold 140 shown in dashed lines for illustrative purposes). Each tubular member 148 may be substantially solid along an inner wall 156 defining a periphery 151 of the tubular member 148 such that the tubular member 148 excludes any bone growth openings along the periphery 151.

Figure 11:
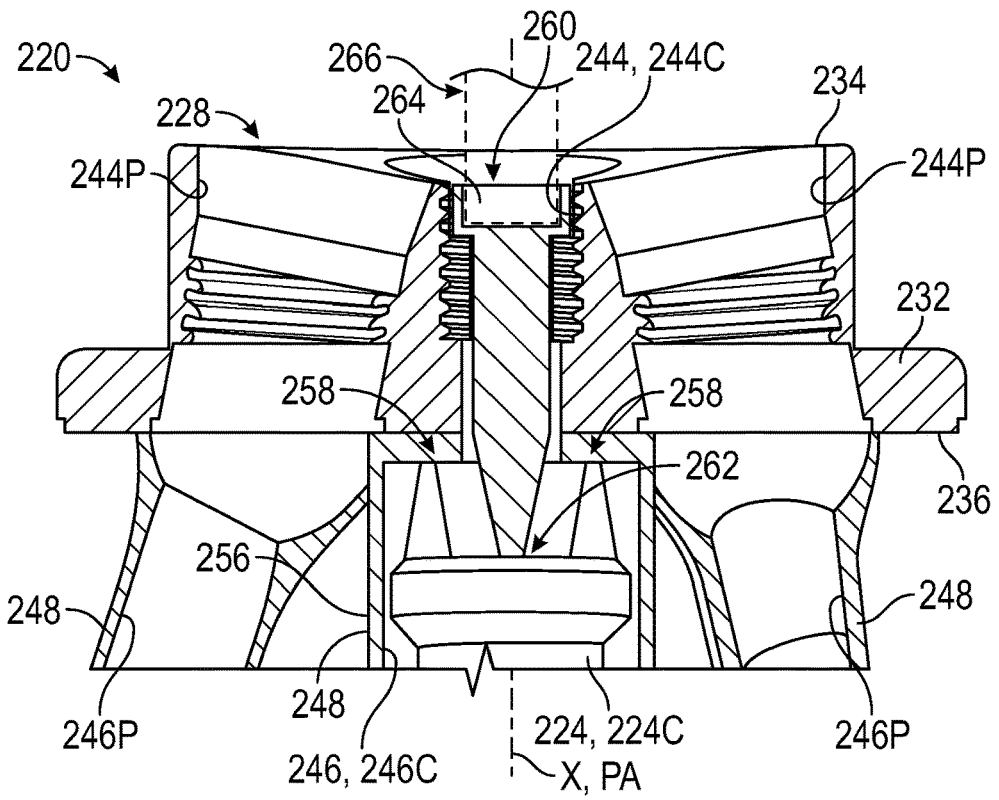
FIGS. 11-13 illustrate sectional views of another exemplary orthopaedic implant including a driving member coupled to a driver.
Figure 12:
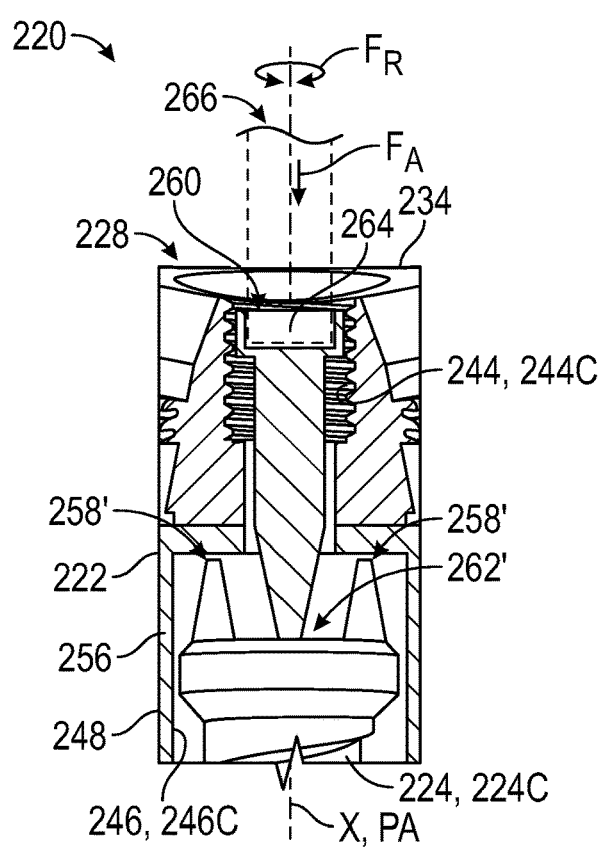
Figure 13:
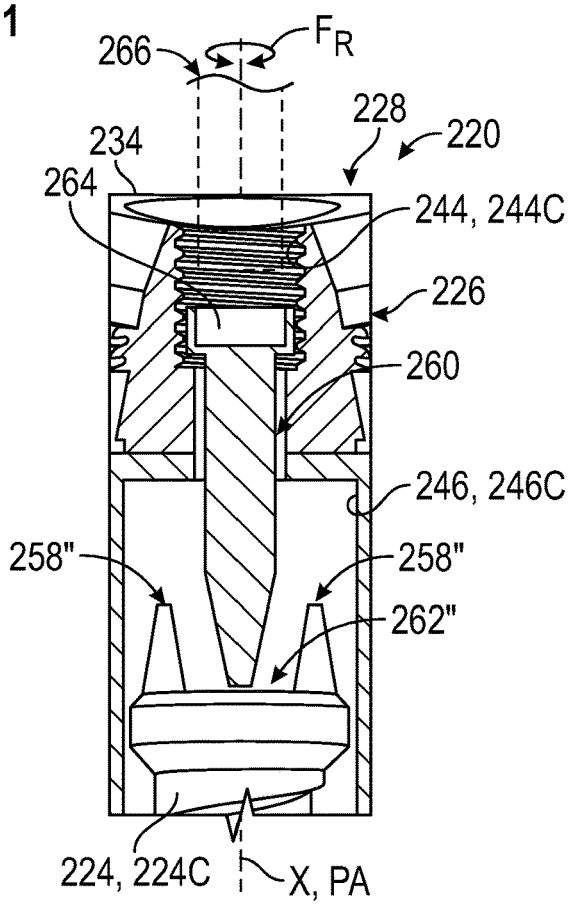

FIGS. 11-12 illustrate another exemplary orthopedic implant 220. FIG. 11 illustrates a non-deployed (e.g., initial) state of the implant 220. The non-deployed state may correspond to a fabricated state of the implant 220 prior to a surgical procedure. FIG. 12 illustrates a first deployed (e.g., interim) state of the implant 220. FIG. 13 illustrates a second deployed state of the implant 220 that differs from the first deployed state. The implant 220 includes a fastener 224 movable between the non-deployed and deployed states such that deployment of the fastener 224 causes a permanent change to the implant 220.

Referring to FIG. 11, the implant 200 may include a driving member 260 coupled to the fastener 224 at a second breakable (e.g., breakaway) connection 262. The second breakable connection 262 may be a frangible connection having a reduced thickness, scoring, perforations, and/or different material compositions (e.g., different densities), etc., to facilitate severing the fastener 224 from the inner wall 256 of the main body 222. The second breakable connection 262 may at least partially extend along a respective passage 246, as illustrated by FIG. 12. The driving member 260 may include an interface 264 dimensioned to engage a driver 266 (showing dashed lines for illustrative purposes). The driver 266 may apply an axial force $F_A$ and/or radial force $F_R$ to the interface 264 to cause a first breakable connection 258 to sever, as illustrated by connection 258' of FIG. 12. The driver 266 may engage the interface 264 to cause the first breakable connection 258 to sever in response to a first predetermined quantity of torque at the interface 264.

The second breakable connection 262 may be dimensioned to sever in response to a second predetermined quantity of torque or force at the interface 264. The second predetermined quantity of torque or force may be greater than the first predetermined quantity of torque or force. For example, the driver 266 may be moved to cause the first breakable connection 258 to sever and then to cause the fastener 224 to move along a respective passage axis PA, as illustrated by first breakable connection 258' in FIG. 12.

The driver 266 may continue to cause the fastener 224 to move along the passage axis PA until the fastener 224 is at a desired position, opposed by another portion of the implant 220, and/or opposed by adjacent bone or other tissue. The driver 266 may continue to apply a force, such as the rotational force $F_R$ until the force $F_R$ exceeds the second predetermined quantity at the interface 264, causing the second breakable connection 262 to sever, as illustrated by a second breakable connection 262" of FIG. 13. The first predetermined quantity of torque may be between 0.25 and 5.0 Newton-meters, such as between 1.0 and 3.0 Newton-meters, and the second predetermined quantity of torque may be between 5.0 and 10.0 Newton-meters, for example.

Various materials may be utilized to form the implants 20, 120, 220 and fasteners 24, 124, 224, including metallic and/or non-metallic materials. The implants 20, 120, 220 and/or fasteners 24, 124, 224 may include one or more coatings or layers deposited along the respective surfaces. Example coatings may include calcium phosphate (CaP) having a porous construction for promoting bone ingrowth.

Figure 14:
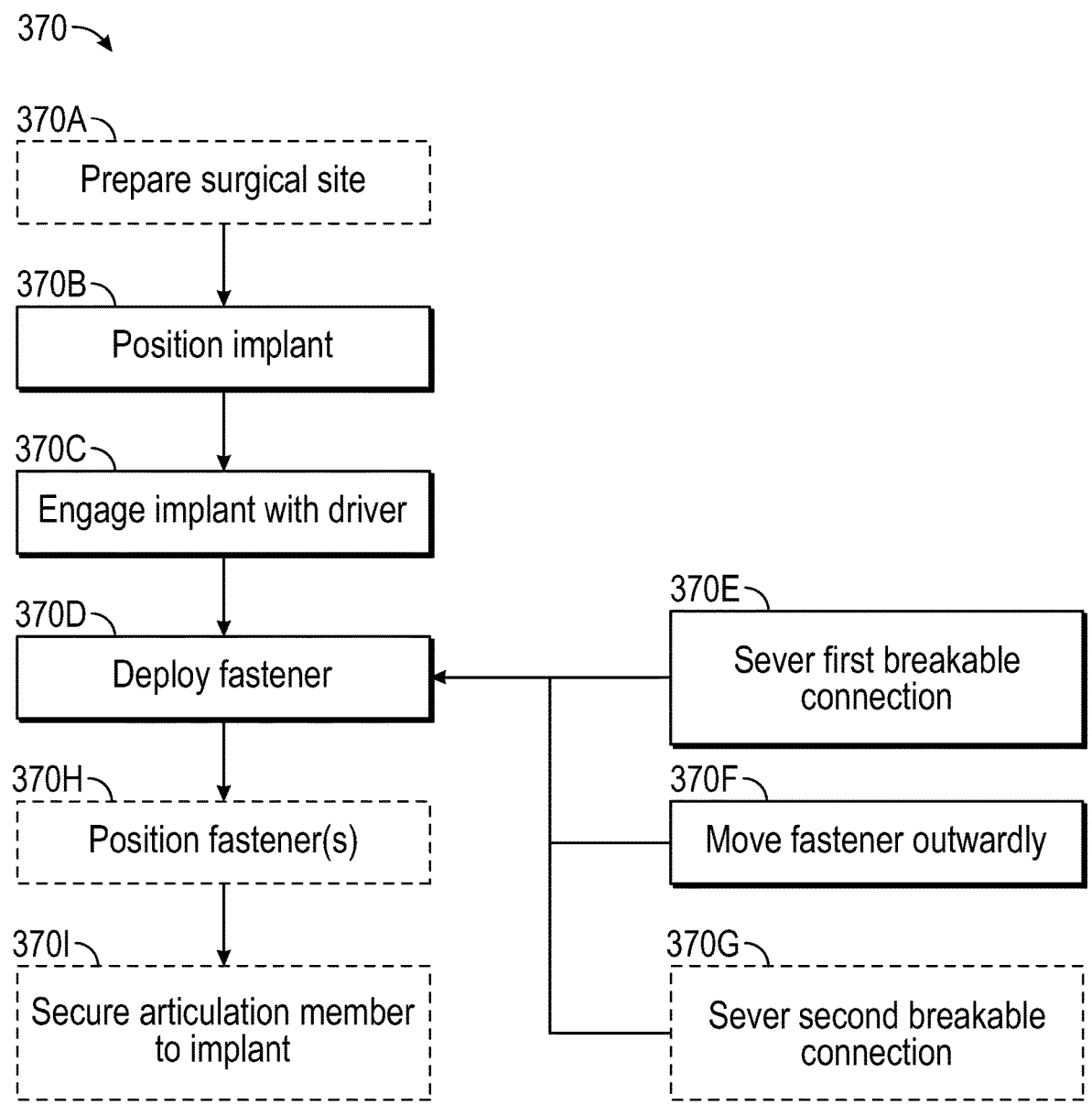
FIG. 14 illustrates an exemplary method of installing an orthopaedic implant at a surgical site.

FIG. 14 illustrates an exemplary method of installing an orthopaedic implant at a surgical site in a flow chart 370. The method may be utilized to perform an arthroplasty for restoring functionality to a joint such as a shoulder having advanced cartilage disease. Although the disclosure primarily refers a glenoid, it should be understood that the method may be utilized to restore functionality to a humerus and other joints of a patient. The method may be utilized with any of the implants disclosed herein. Fewer or additional steps than are recited below could be performed within the scope of this disclosure, and any recited order of the steps is not intended to limit this disclosure.

Figure 15:
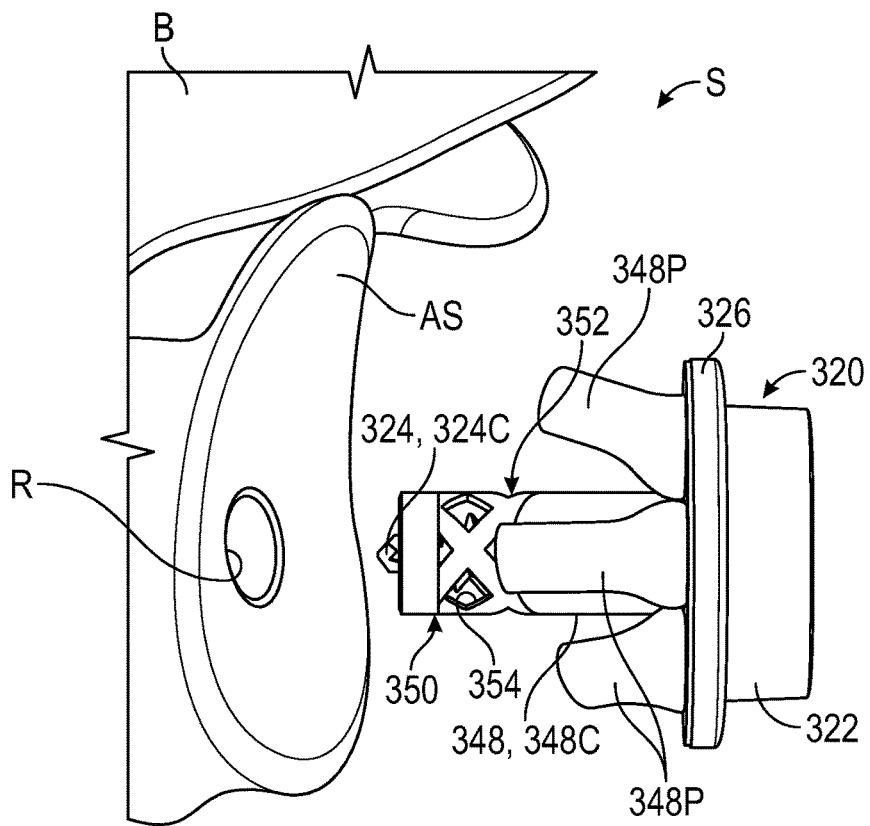
FIGS. 15-20 illustrate various steps of installing an orthopaedic implant which may be associated with the method of FIG. 14.

Referring to FIG. 15, with continuing reference to FIG. 14, a surgical site S may be prepared for receiving an implant 320 at step 370A. The implant 320 may incorporate the features of the implant 120, for example. Step 370A may include performing one or more operations to prepare the surgical site S such as one or more reaming, milling and drilling operations to establish a desired geometry of the surgical site S. Step 370A may include forming at least one or more recesses R at the surgical site S. Step 370A may include forming each recess R in an articular surface AS of the bone B by removing tissue such as a portion of the bone B. The recess R may be dimensioned to at least partially receive a portion of a tubular member 348 of the implant 320, such as the central tubular member 348C. The bone B may include an articular surface AS of a glenoid. The articular surface AS may have a relatively lesser concavity than an articular surface AS of FIGS. 21-23, for example.

Figure 16:
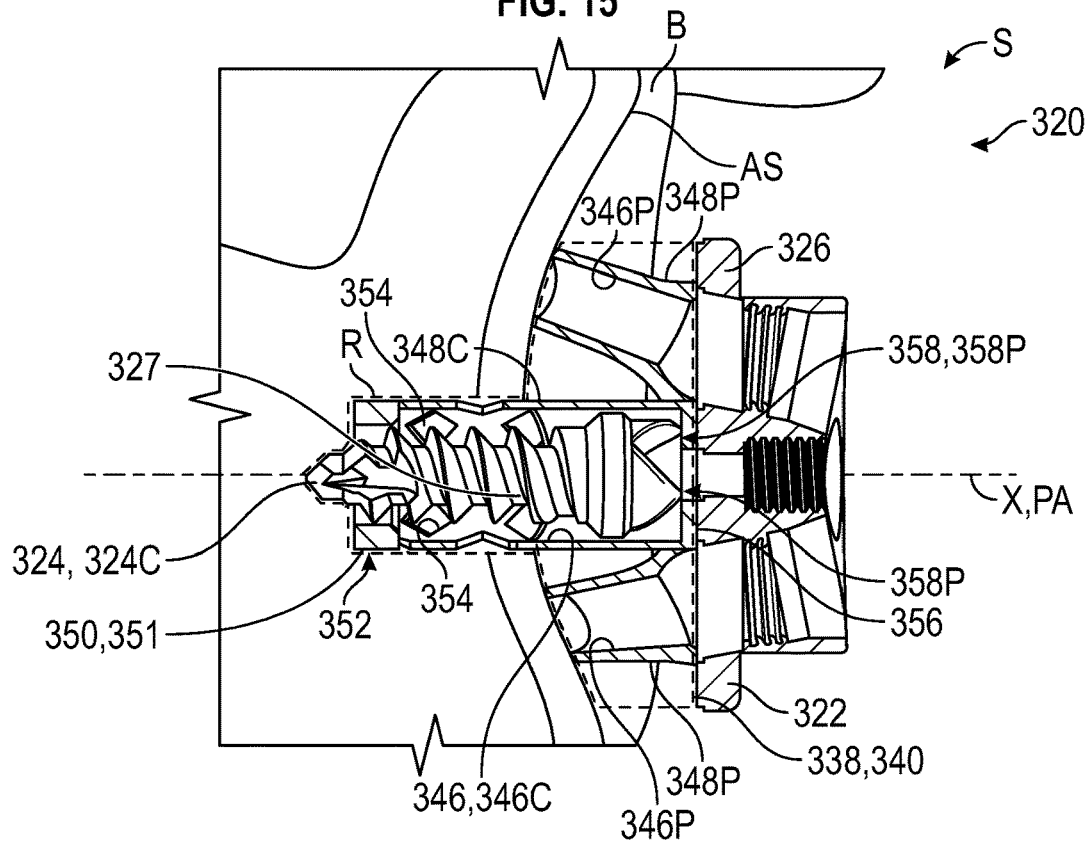

Referring to FIG. 16, with continuing reference to FIGS. 14-15, at step 370B the implant 320 may be positioned adjacent to and along the bone B at the surgical site S. The implant 320 may include a main body 322 establishing one or more passages 346 including a central passage 346C that extends along a longitudinal axis X of the implant 320. The implant 320 may include an augment body 338 established by a scaffold 340 (shown in dashed lines in FIG. 16 and omitted from FIGS. 17-20 for illustrative purposes). Step 370B may include positioning the implant 320 such that the scaffold 340 abuts against bone B and/or other tissue along the articular surface AS, as illustrated in FIG. 16. The implant 320 may include at least one fastener 324 coupled to an internal wall 356 of the main body 322 at a first breakable connection 358 along the respective passage 346. The first breakable connection 358 may include a plurality of breakable connection points 358P integrally formed with the main body 322 of the implant 320 along the passage 346, as illustrated in FIG. 16.

Figure 32:
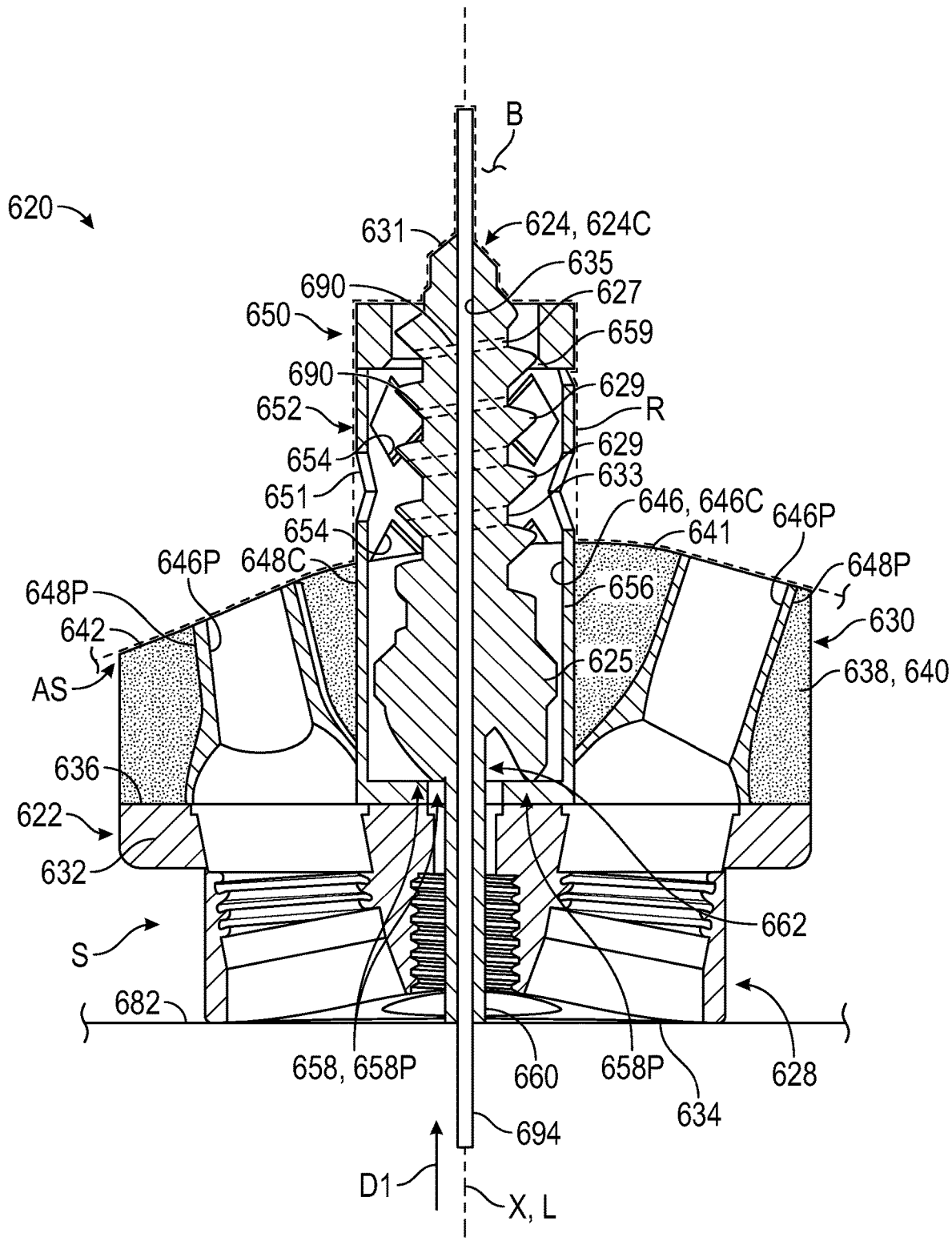

At least one of the tubular members 348 may be positioned in contact with the articular surface AS of the bone B, such as peripheral tubular members 348P. The central tubular member 348C may be positioned and at least partially received in the respective recess R (indicated in dashed lines in FIG. 16-18 for illustrative purposes) such that the tubular member 348C serves as an anchoring stem 350 for securing the implant 320 to the bone B. The recess R may include a first section dimensioned to substantially compliment a periphery 351 of the respective tubular member 348 and a second section that substantially compliments a geometry of a shank portion 327 of the fastener 324, as illustrated in FIG. 18. A portion of the anchoring stem 350 may include a cage 352 or another structure establishing one or more bone growth openings 354. Positioning the implant 320 may include positioning at least the portion of the anchoring stem 350 defining the bone growth openings 354 in the recess R. The bone growth openings 354 may be positioned to face towards surfaces of the bone B bounding the recess R to promote bone ingrowth and additional fixation of the implant 320. In some implementations, step 370B may include positioning a guide wire 694 in bone B, inserting the guide wire 694 in a passage 635 established by a cannulated fastener 624, and then moving implant 620 in a direction D1 along the guide wire 694 to abut against an articular surface AS of the bone B, as illustrated in FIG. 32 (surface AS and recess R shown in dashed lines for illustrative purposes).

Figure 17:
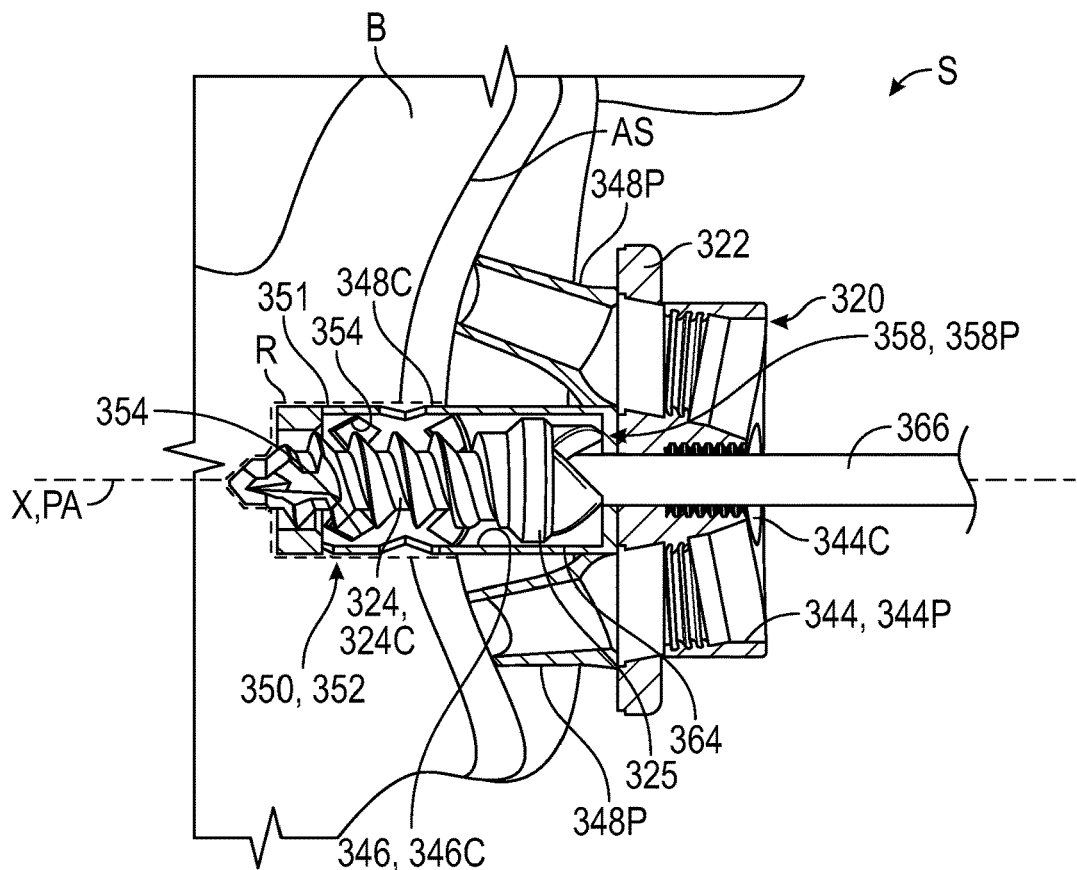
Figure 18:
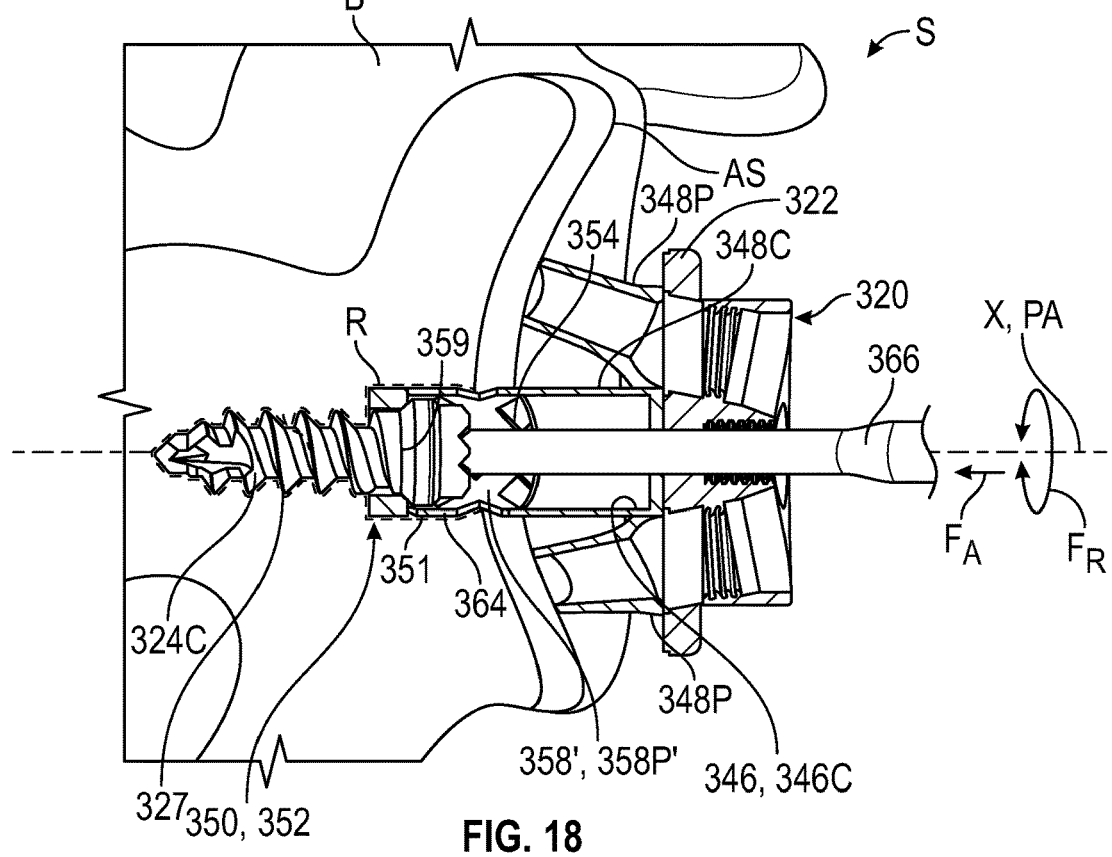

Referring to FIG. 17, with continuing reference to FIG. 14, at step 370C the surgeon may move a driver 366 into engagement with an interface 364 of the implant 320 to deploy the respective fastener 324. The interface 364 may have various configurations for engagement with the driver 366, such as a socket connection.

Referring to FIG. 18, with continuing reference to FIG. 14, at step 370D the surgeon may cause the driver 366 to apply a force at the interface 364 to deploy the fastener 324. Step 370D may include severing the first breakable connection 358 at step 370E, as illustrated by first breakable connection 358'. Step 370E may include applying an axial force $F_A$ and/or rotational force $F_R$ to the interface 364 relative to the respective passage axis PA and/or longitudinal axis X of the implant 320 to sever the breakable connection points 358P of the first breakable connection 358 and deploy the fastener 324. Applying the axial force $F_A$ may include moving the driver 366 a distance along the passage axis PA. Applying the rotational force $F_R$ may include rotating the driver 366 circumferentially about the passage axis PA. Severing the first breakable connection 358 may include causing the driver 366 to apply a first torque at the interface 364 that exceeds a first predetermined quantity of torque. The first predetermined quantity of torque may include any of the quantities disclosed herein.

Severing the first breakable connection 358 may occur such that the severing action generates an indicator such as an audible click and/or tactile force which may be observable by the surgeon. The audible click may provide an indicator or feedback to the surgeon during installation of the implant 320 indicating that the implant 320 is no longer in the non-deployed state.

Step 370D may include moving the driver 366 axially along the passage axis PA at step 370F to cause the fastener 324 to move at least partially outwardly from the respective passage 346 and into the bone B to secure the implant 320 at the surgical site S. Step 370F may occur subsequent to step 370E.

In some implementations, the method 370 may include utilizing a driving member to establish the interface. Referring to FIGS. 11-13, with continuing reference to FIG. 14, the method 370 may include severing the second breakable connection 262 at step 370G. Step 370G may occur subsequent to severing the first breakable connection 258 at step 370E. Severing the second breakable connection 262 may occur in response to causing the driver 266 to apply a second torque at the interface 264. Severing the second breakable connection 262 may occur such that the severing generates an audible click. The audible click may provide an indicator or feedback to the surgeon during installation of the implant 220 indicating that the implant 220 is no longer in the non-deployed state.

Severing the second breakable connection 262 may occur in response to causing the driver 266 to apply a second torque at the interface 264 that exceeds a second predetermined quantity torque to sever the second breakable connection 262, as illustrated by the second breakable connection 262" of FIG. 13. The second predetermined torque may be greater than the first predetermined quantity of torque such that the first breakable connection 258 severs prior to the severing of the second breakable connection 262. The second breakable connection 262 may serve as a torque limiter to reduce a likelihood of applying excessive torque to the fastener 324, which may otherwise cause the threads to lose fixation with the adjacent bone.

Figure 19:
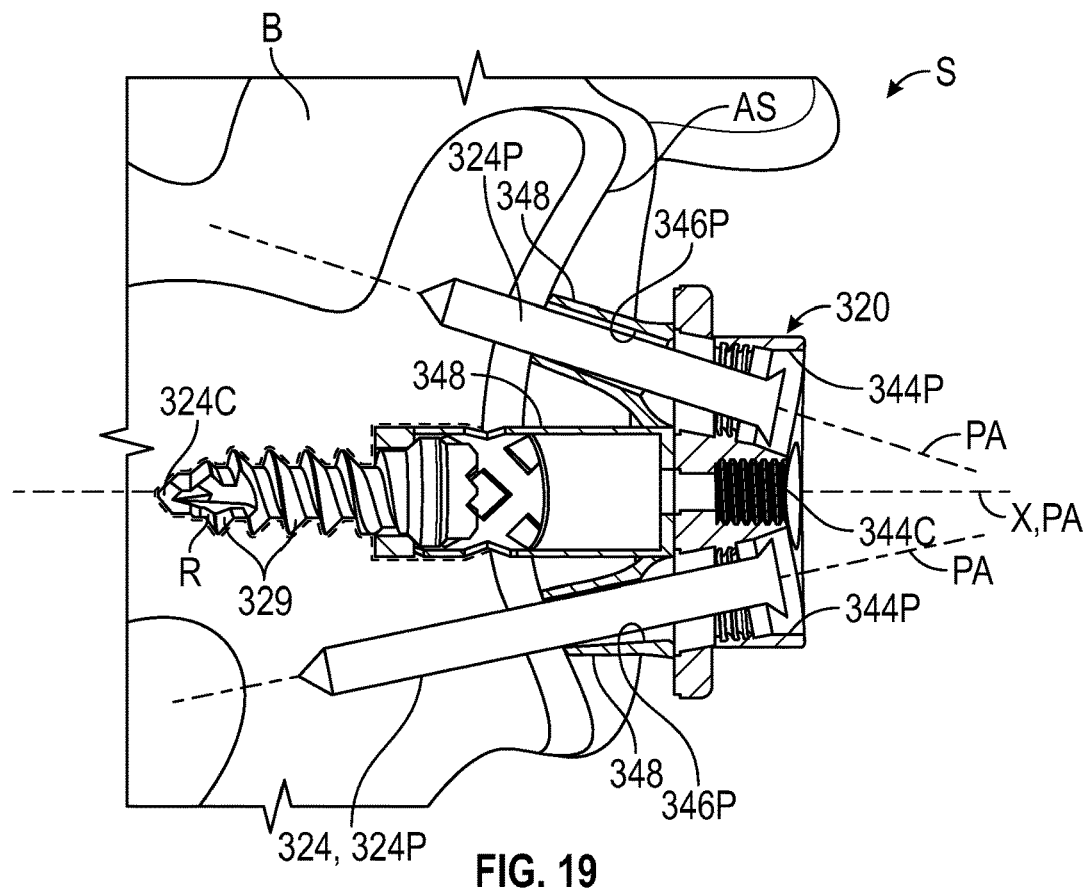

Referring to FIG. 19, with continuing reference to FIG. 14, the driver 366 may be removed from the interface 364 subsequent to step 370D. At step 370H, one or more other fasteners 324 may be positioned at least partially through the implant 320 and into the bone B to secure the implant 320 at the surgical site S. The fasteners 324 may include any of the fasteners disclosed herein including compression screws. In implementations, the fasteners 324 may include peripheral fasteners 324P positioned at least partially into the respective peripheral apertures 344P and peripheral passages 346P and then into the bone B to secure the implant 320.

Figure 20:
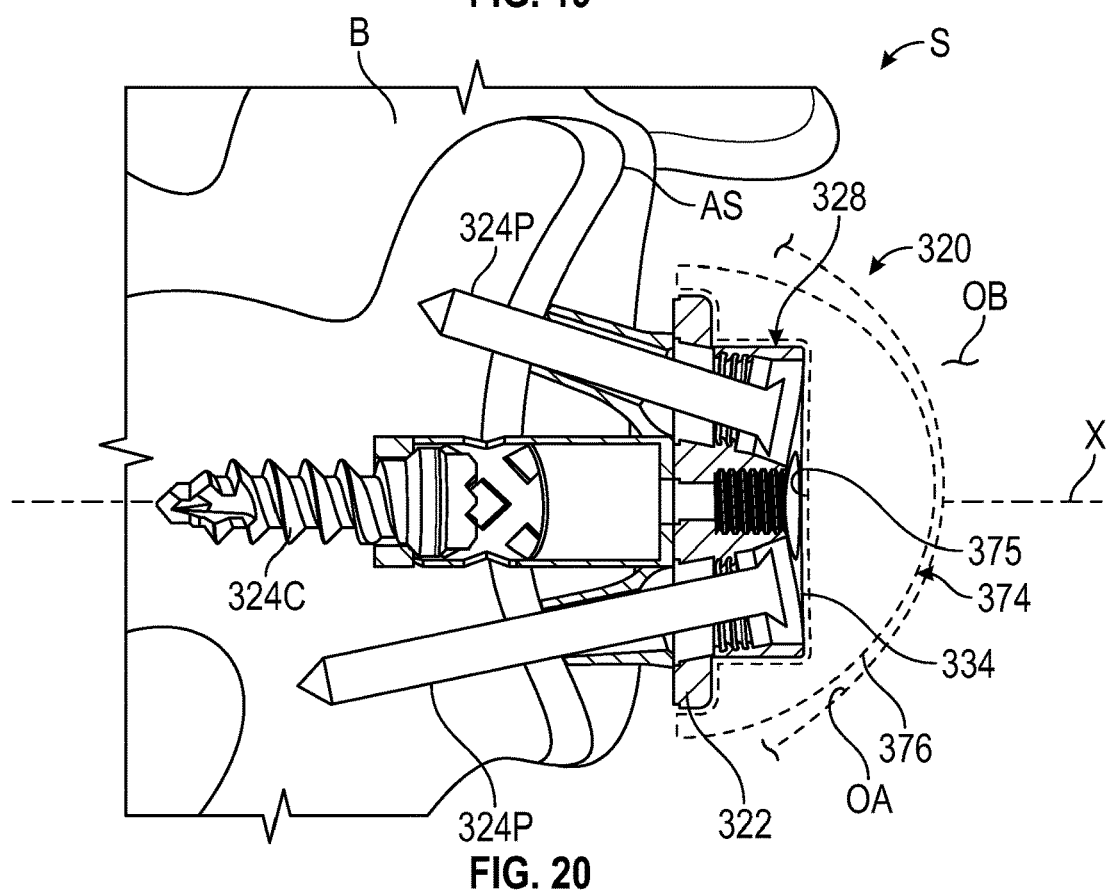

Referring to FIG. 20, with continuing reference to FIG. 14, the method may include securing an articulation member 374 to the main body 322 of the implant 320 at step 370I. The articulation member 374 is illustrated in dashed lines for illustrative purposes. Step 370I may include mechanically attaching or releasably securing the articulation member 374 to a first (e.g., front) face 334 of the baseplate 328. The articulation member 374 may include a recess 375 dimensioned to receive a portion of the baseplate 328. A perimeter of the baseplate 328 may be dimensioned to cooperate with a perimeter of the recess 375 to establish a Morse taper connection. The articulation member 374 may be impacted onto the baseplate 328 to establish the Morse taper connection and secure the articulation member 374.

The articulation member 374 may include an articulation surface 376 dimensioned to mate with an opposed articular surface OA (shown in dashed lines for illustrative purposes). The articular surface OA may be associated with an adjacent bone OB at the surgical site S, such as a humerus or another bone forming the respective joint. The articular surface OA may be established by a bone surface and/or an opposed implant. The articulation surface 376 may have various geometries that complement a geometry of the opposed articular surface OA, such as a generally concave geometry or a generally convex geometry as illustrated in FIG. 20.

Figure 21:
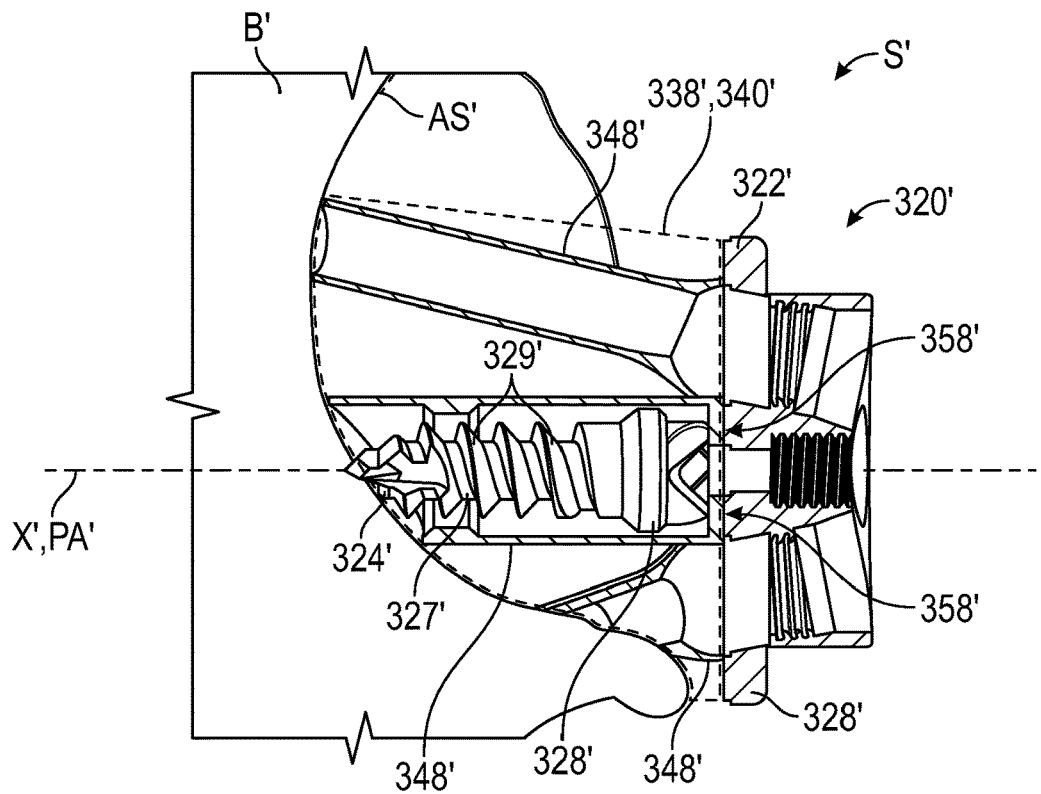
FIGS. 21-23 illustrates various steps of installing another orthopaedic implant which may be associated with the method of FIG. 14.
Figure 22:
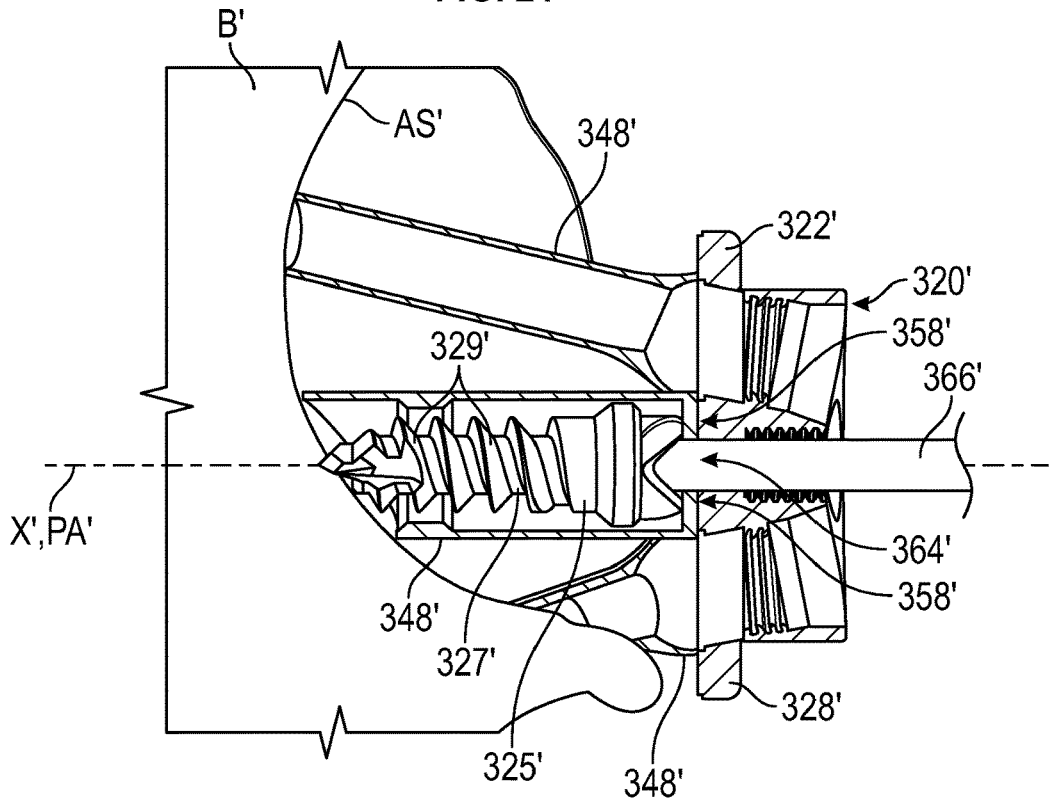
Figure 23:
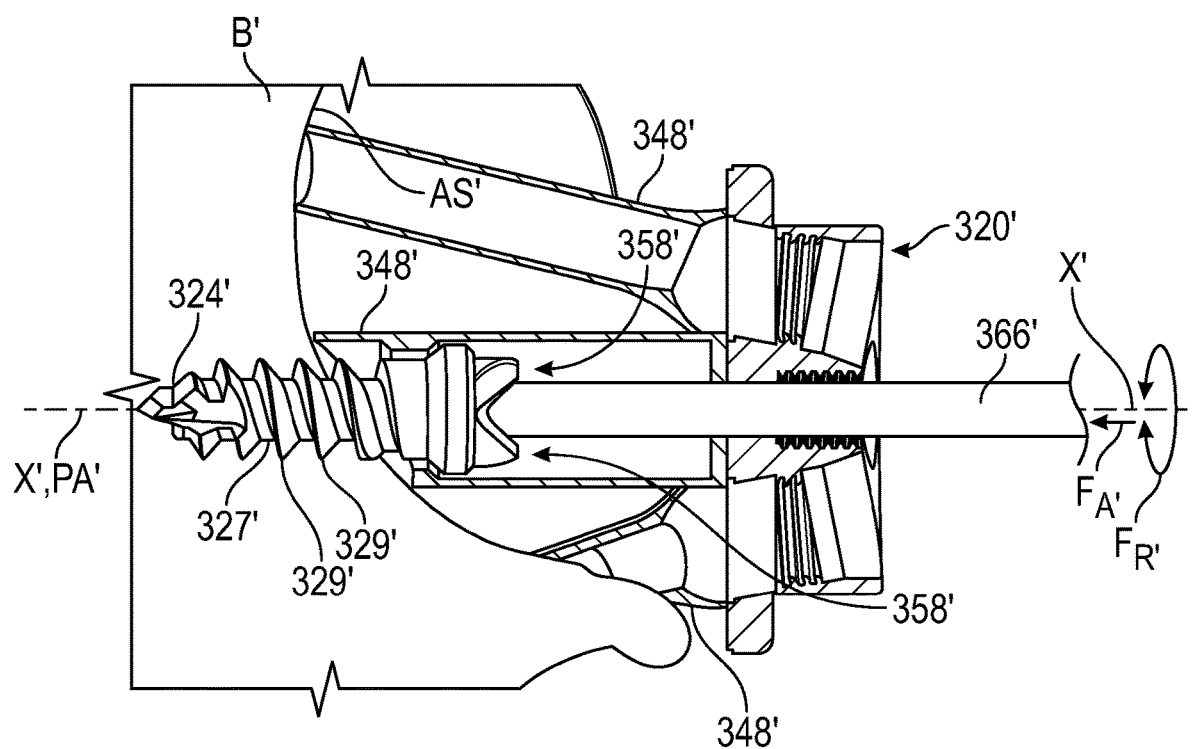

Referring to FIGS. 21-23, with continuing reference to FIG. 14, bone growth openings in tubular members 348' may be omitted. Step 370B may include positioning the tubular members 348' in abutment with an articular surface AS of the respective bone B. The implant 320' may include an augment body 338' established by a scaffold 340' (shown in dashed lines in FIG. 21 and omitted from FIGS. 22-23 for illustrative purposes). Step 370B may include positioning the implant 320' such that the scaffold 340' abuts against bone B and/or other tissue along the articular surface AS, as illustrated in FIG. 21. Referring to FIG. 23, a driver 366' may apply an axial force $F_A$ and/or rotational force $F_R$ relative to the passage axis PA to at least partially drive the respective fastener 324 into the bone B.

Figure 24:
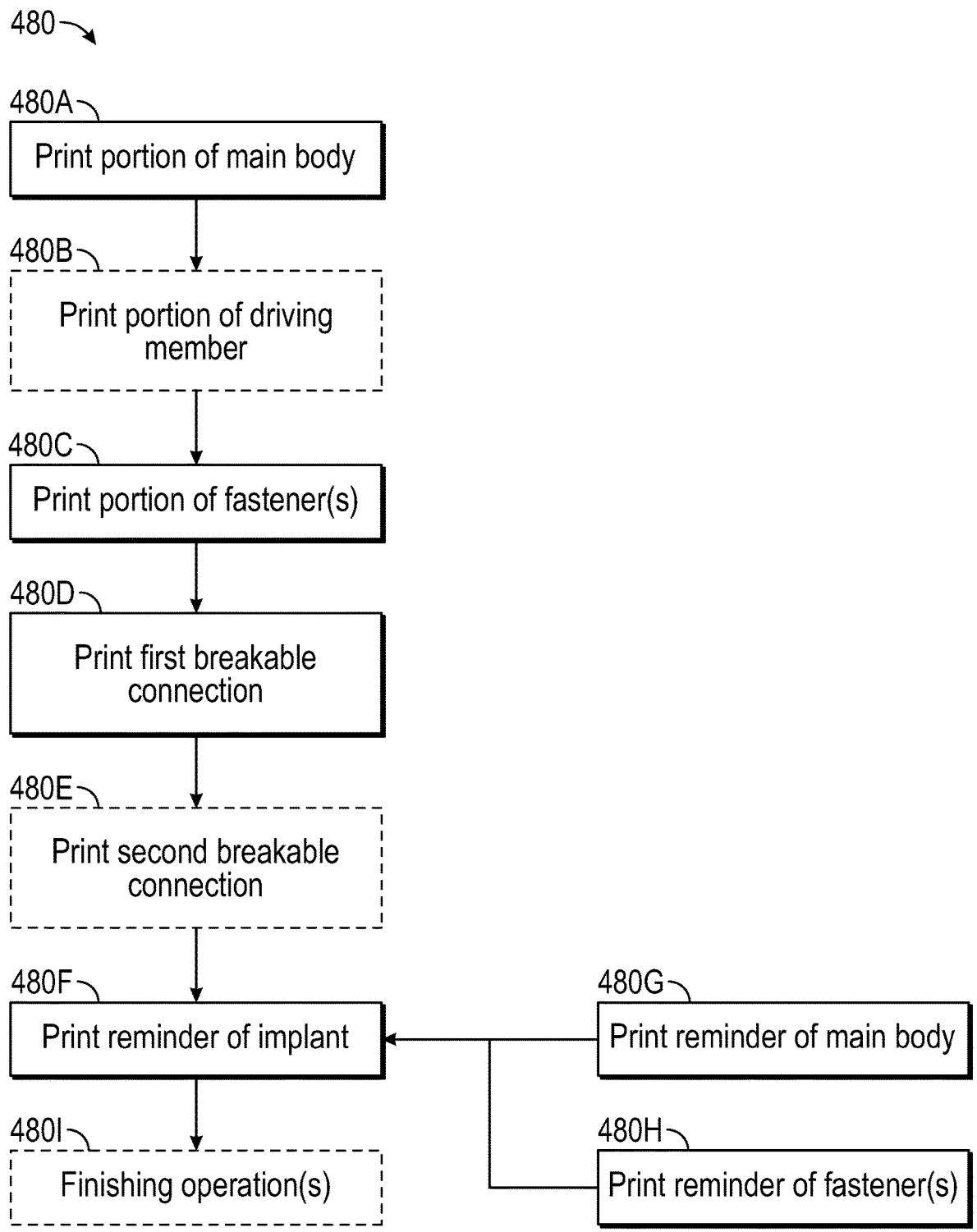
FIG. 24 illustrates an exemplary method of forming an orthopaedic implant.

FIG. 24 illustrates an exemplary method of forming an orthopaedic implant in a flow chart 480. The method may be utilized to form any of the implants disclosed herein, including the implants 20, 120, 220 and/or 320. Fewer or additional steps than are recited below could be performed within the scope of this disclosure, and any recited order of the steps is not intended to limit this disclosure.

Figure 25:
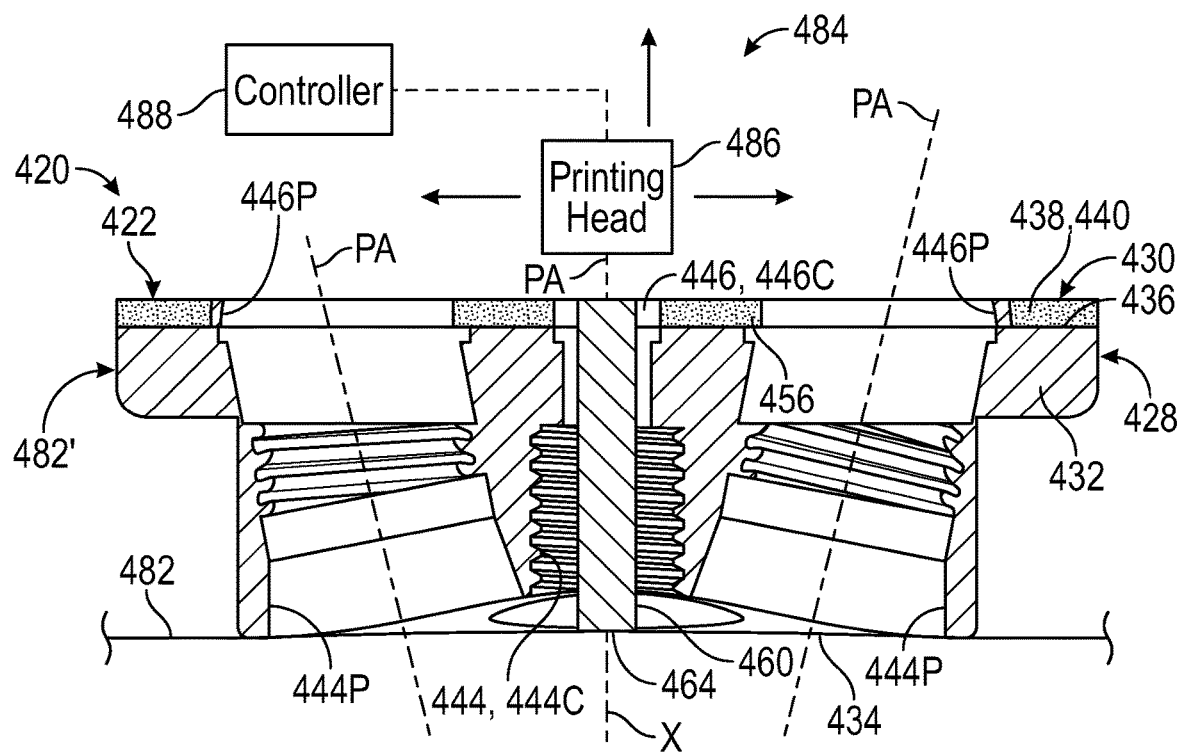
FIGS. 25-30 illustrates sectional views of various states of formation of an exemplary orthopaedic implant which may be associated with the method of FIG. 24.

Referring to FIG. 25, with continuing reference to FIG. 24, various techniques may be utilized to form an implant 420. The method may utilize a printing assembly 484 to form the implant 420. The printing assembly 484 may incorporate a three-dimensional (3D) printing head 486 coupled to a controller 488. The controller 488 may be operable to obtain coordinate information corresponding to a predetermined geometry of the implant 420 and may be operable to command the printing head 486 to perform a series of passes to form successive layers of material on a substrate 482. The printing assembly 484 may be operable to form the implant 420 utilizing any of the materials disclosed herein, including metallic and/or non-metallic materials. Three-dimensional printers are known, but utilization of three-dimensional printers to form the disclosed implants is not known.

At step 480A, the printing assembly 484 may print or otherwise form a portion of a main body 422 of the implant 420 on the substrate 482. The main body 422 may include a baseplate 428 and an augment 430 extending from the baseplate 428. The substrate 482 may be separate and distinct from the implant 420. In some implementations, substrate 482' is a prefabricated portion of the implant 420, such as the baseplate 428. The baseplate 428 may include a plate body 432 extending between a first (e.g., front) face 434 and a second (e.g., rear) face 436 along a longitudinal axis X of the implant 420.

Step 480A may include printing the plate body 432 of the baseplate 428 to establish one or more apertures 444. The apertures 444 may include a central aperture 444C and one or more peripheral apertures 444P extending between the front face 434 and the rear face 436 of the plate body 432.

Step 480A may including printing the portion of the main body 422 to include an inner wall 456 establishing one or more passages 446. The passages 446 may include a central passage 446C and one or more peripheral passages 446P. The central aperture 444C may extend along the longitudinal axis X between the front face 434 and the central passage 446C. The peripheral apertures 444P may be circumferentially distributed about the longitudinal axis X.

Figure 30:
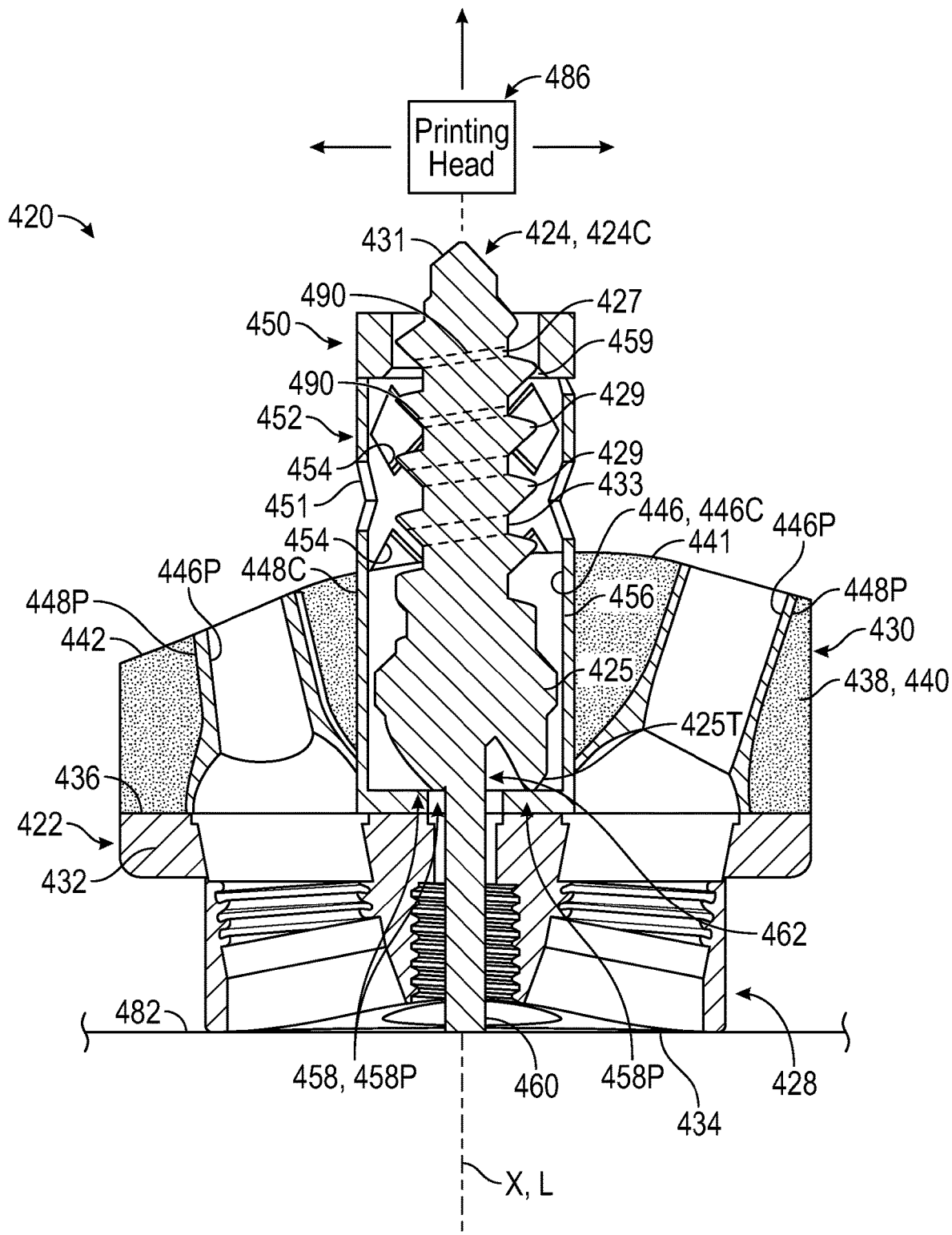

Step 480A may include printing an augment 430 including an augment body 438 onto the rear face 436 of the baseplate 428. The augment body 438 may be dimensioned to contact bone. The peripheral passages 446P may be at least partially aligned with respective ones of the peripheral apertures 444P along the passage axes PA. Each of the peripheral passages 446P may extend between the rear face 436 of the baseplate 428 and an external surface 442 of the implant 420 along the a second (e.g., rear) face 441 of the augment 430, as illustrated in FIG. 30. Each respective pair of the peripheral apertures 444P and peripheral passages 446P may be dimensioned to at least partially receive a respective fastener along a passage axis PA, with each respective fastener dimensioned to be partially received in bone (see, e.g., FIGS. 19-20).

Figure 26:
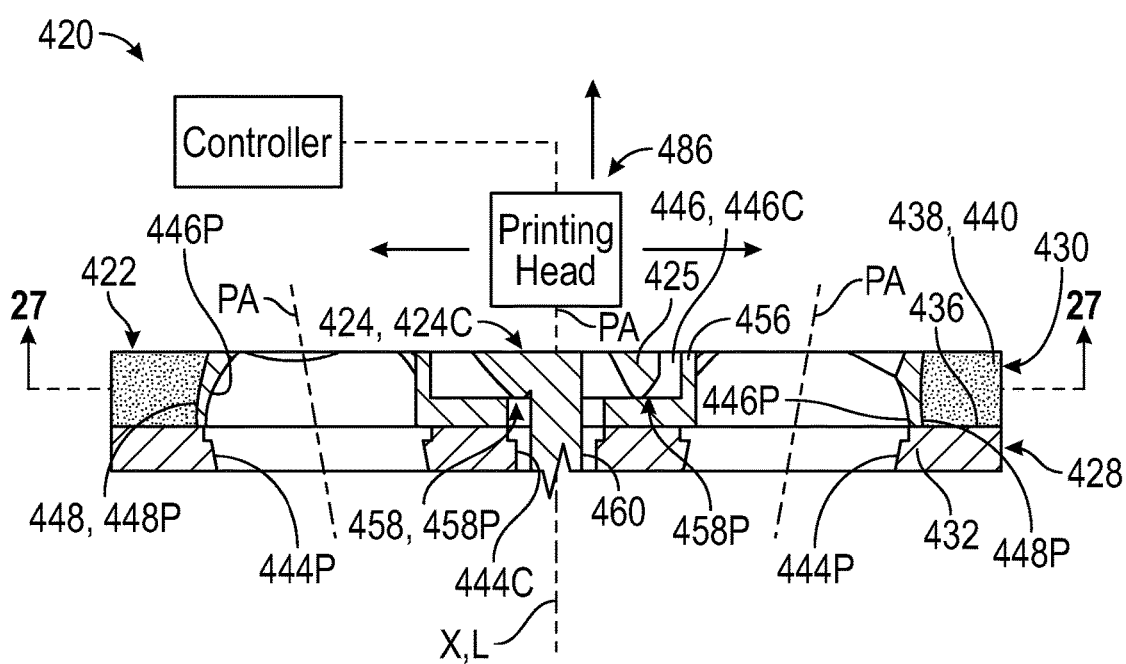
Figure 28:
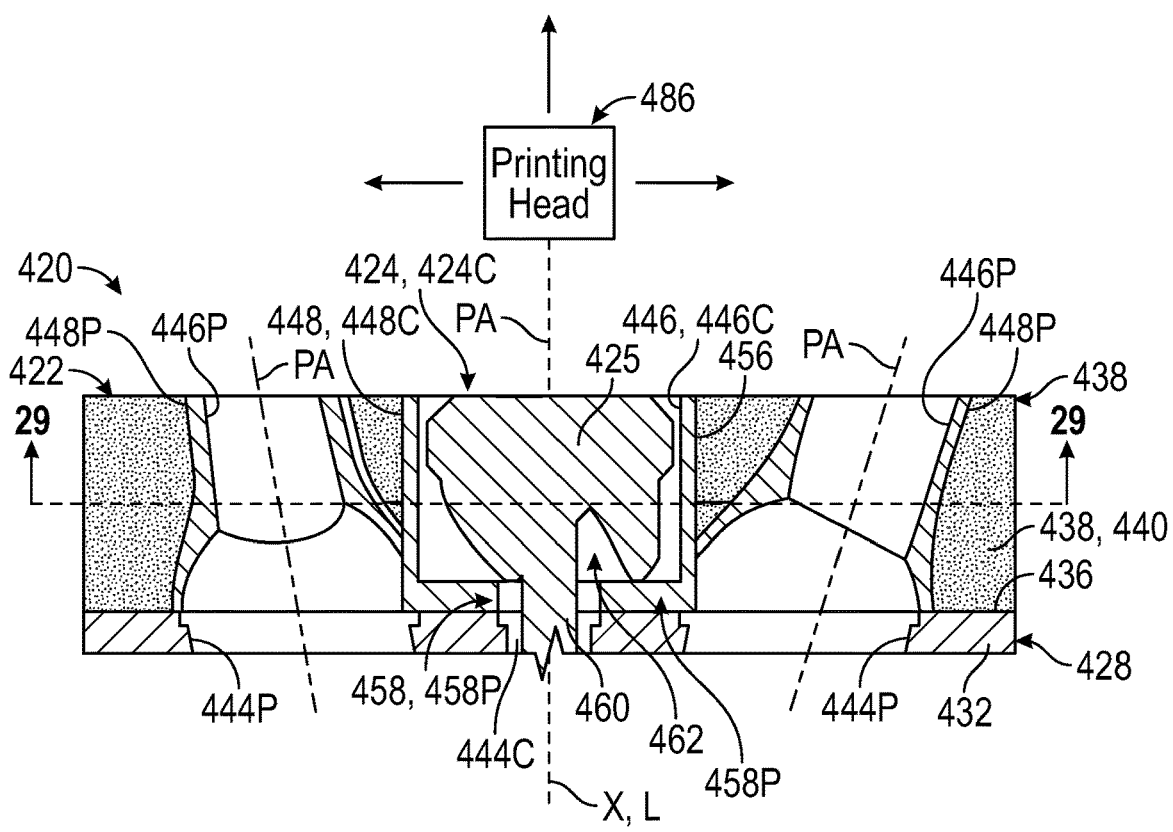

Step 480A may include printing one or more tubular members 448 that establish the respective passages 446, as illustrated in FIGS. 26, 28 and 30. The tubular members 448 may include a central tubular member 448C and one or more peripheral tubular members 448P circumferentially distributed about the central tubular member 448C relative to the longitudinal axis X. The augment body 438 may include a porous scaffold 440 that at least partially surrounds the tubular members 448. The scaffold 440 may establish an external surface of the augment 430. In some implementations, the augment body 438 is substantially solid.

The method may include printing or otherwise forming at least a portion of a driving member 460 at step 480B. The driving member 460 may include an interface 464 dimensioned to engage a driver (see, e.g., FIGS. 11-13). At least a portion of the driving member 460 may be formed along one of the apertures 444 and/or passages 446, such as the central aperture 444C and/or central passage 446C. In some implementations, the driving member 460 is omitted.

Referring to FIG. 26, with continuing reference to FIGS. 24-25, a portion of at least one fastener 424 is printed or otherwise formed at step 480C. Step 480C may be separately performed, or may be concurrently performed with steps 480A and/or 480B, for example. Step 480C may include printing the fastener 424 at least partially in a volume of the respective passage 446. The fastener 424 may be dimensioned to be at least partially received in bone and may include any of the fasteners disclosed herein. The fastener 424 may include a central fastener 424C printed at least partially in the central passage 446C, for example. Each fastener 424 and respective passage axis PA may be dimensioned with respect to a predetermined geometry and/or predetermined orientation. The predetermined geometry and/or predetermined orientation may be patient-specific based on a preoperative surgical plan based on one or more measurements of the patient determined prior to formation of the implant 420. The patient-specific geometry may provide a fastener 424 having a length and orientation that substantially complements a profile and quality of the bone of the patient and may facilitate positioning of the implant 420 during surgery.

Figure 27:
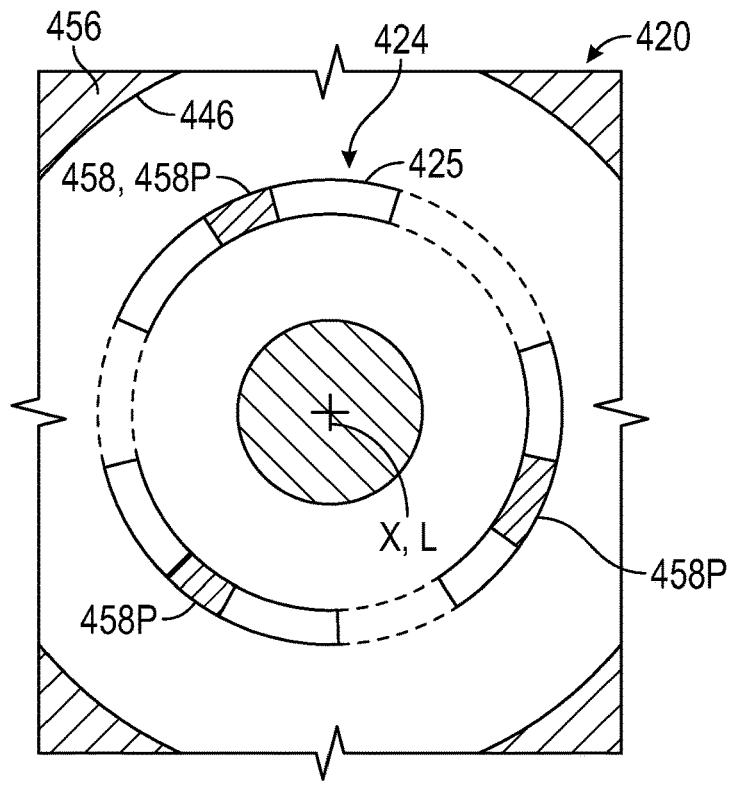

At step 480D, a first breakable connection 458 is printed or otherwise formed. The first breakable connection 458 may be integrally formed with and interconnects the internal wall 456 of the main body 422 and the fastener 424. The first breakable connection 458 can include a plurality of separate and distinct breakable connection points 458P circumferentially distributed about a longitudinal axis L of the fastener 424, as illustrated in FIG. 27. Although FIG. 27 illustrates the first breakable connection 458 established by a total of three breakable connection points 458P, it should be understood that the implant 420 may have fewer or more than three breakable connection points 458P to establish the first breakable connection 458, such as only one or two breakable connection points 458P. Utilizing a plurality of breakable connection points 458P may provide improved control of placement and stability of the fastener 424 during formation of the implant 420 and prior to severing the first breakable connection 458. The longitudinal axis L of the fastener 424 may be collinear with or otherwise parallel to the longitudinal axis X of the implant 420. The interface 464 may be dimensioned to engage a driver to cause the first breakable connection 458 to sever in response to a first predetermined quantity of torque or force at the interface 464. The fastener 424 may be formed such that a portion of the fastener 424 is moveable outwardly from the passage 446 in response to severing the first breakable connection 458.

Figure 29:
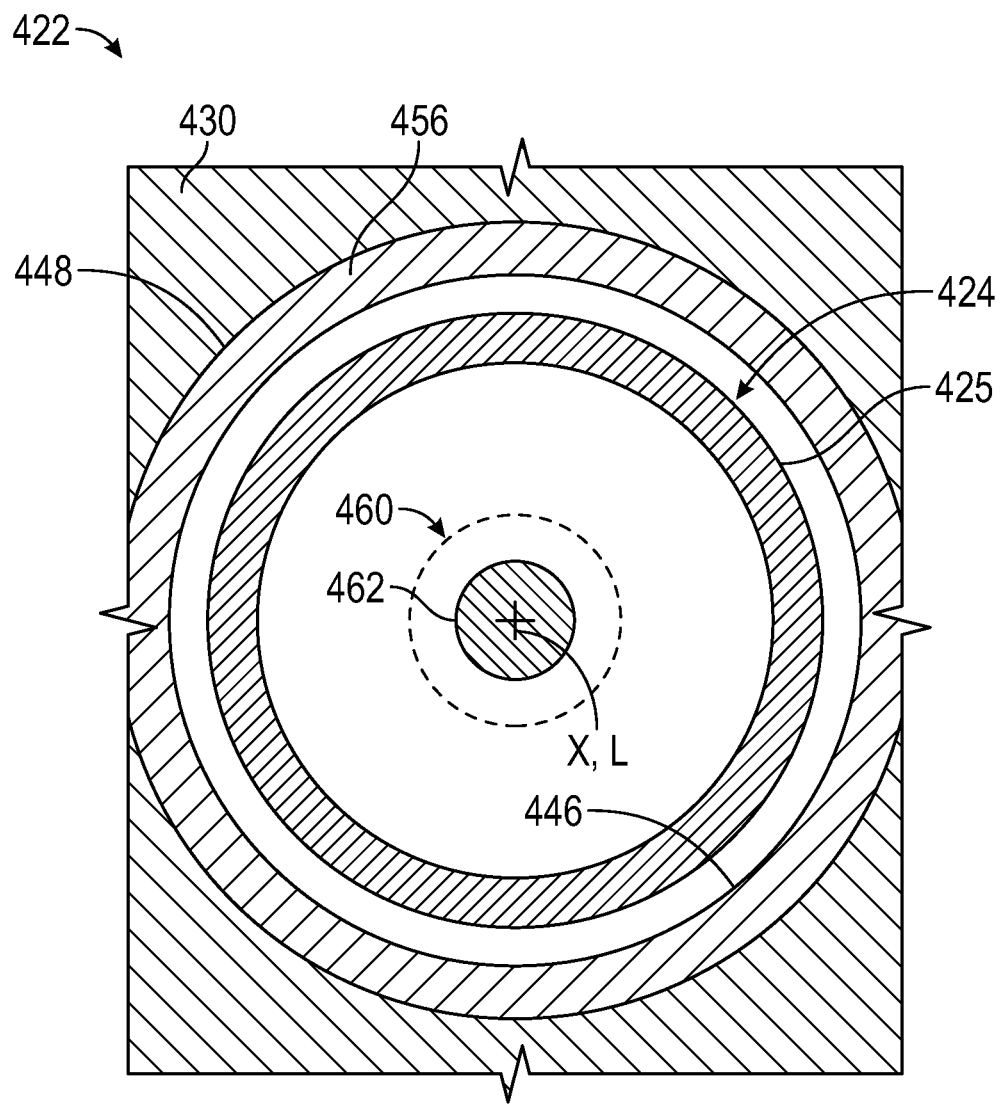

Referring to FIGS. 28-29, with continuing reference to FIG. 24, the method may include printing or otherwise forming a remainder of the driving member 460 including a second breakable connection 462 at step 480E. The second breakable connection 462 is integrally formed with and interconnects the driving member 460 and the head portion 425 of the fastener 424, as illustrated in FIG. 29. At least a portion of the second breakable connection 462 may be established along the passage 446. The second breakable connection 462 may be dimensioned to sever in response to a second predetermined quantity of torque or force at the interface 464 (FIG. 25). The second predetermined quantity of torque or force may be greater than the first predetermined quantity of torque or force. The second predetermined quantity of torque or force may be based on a bone density or quality of the bone of the respective patient determined prior to formation of the implant 420.

In implementations, the implant may be formed such that the fastener is cannulated. Referring to FIG. 32, various steps of the method 480, such as steps 480C and/or 480H, may be performed such that fastener 624 is cannulated. A passage 635 may be established along a longitudinal axis X of the implant 620. The passage 635 may extend through the fastener 624 and/or driving member 660 and may be dimensioned to at least partially receive a guide wire 694. The guide wire 694 may be at least partially received in bone B inwardly of a recess R (shown in dashed lines for illustrative purposes) to position and/or orient the fastener 624 relative to the surgical site S.

Various techniques may be utilized to establish each frangible connection point of the first breakable connection 458 and/or second breakable connection 462 at steps 480D-480E. Step 480D and/or step 480E may be performed such that each frangible connection point of the first breakable connection 458 and/or second breakable connection 462 is established by a reduced thickness, scoring, perforations, and/or different material compositions (e.g., different densities), etc., to facilitate severing the fastener 424 from the main body 422 and/or driving member 460.

FIGS. 33-35 illustrate exemplary techniques for establishing frangible connection points of any of the breakable connections disclosed herein, including the first and/or second breakable connections. Referring to FIG. 33, breakable connection 758/762 may be established by a first width W1 along a portion of an inner wall 756 and/or driving member 760 and a second width W2 along a portion of a fastener 724, such as an end portion or periphery of a head portion 725 or shank portion 727 of the fastener 724. The first width W1 may be different from the second width W2 such that the breakable connection 758/762 has a reduced thickness along a portion of the breakable connection 758/762. Referring to FIG. 34, breakable connection 858/862 may have one or more perforations 892 extending at least partially or completely through a thickness of the breakable connection 858/862. The breakable connection 858/862 may have one or more scores 894 extending at least partially or completely about a periphery of the breakable connection 858/862. Referring to FIG. 35, a portion of an inner wall 956 and/or driving member 960 directly coupled to breakable connection 958/962 may be made of a first material M1, the breakable connection 958/962 may be may be made of a second material M2, and a portion of fastener 924 directly coupled to the breakable connection 958/962 may be made of a third material M3. The second material M2 may differ from the first material M1 and/or the third material M3 to establish a frangible connection point. For example, the second material M2 may have a density that is less than or otherwise differs from the first material M1 and/or third material M3.

Figure 36:
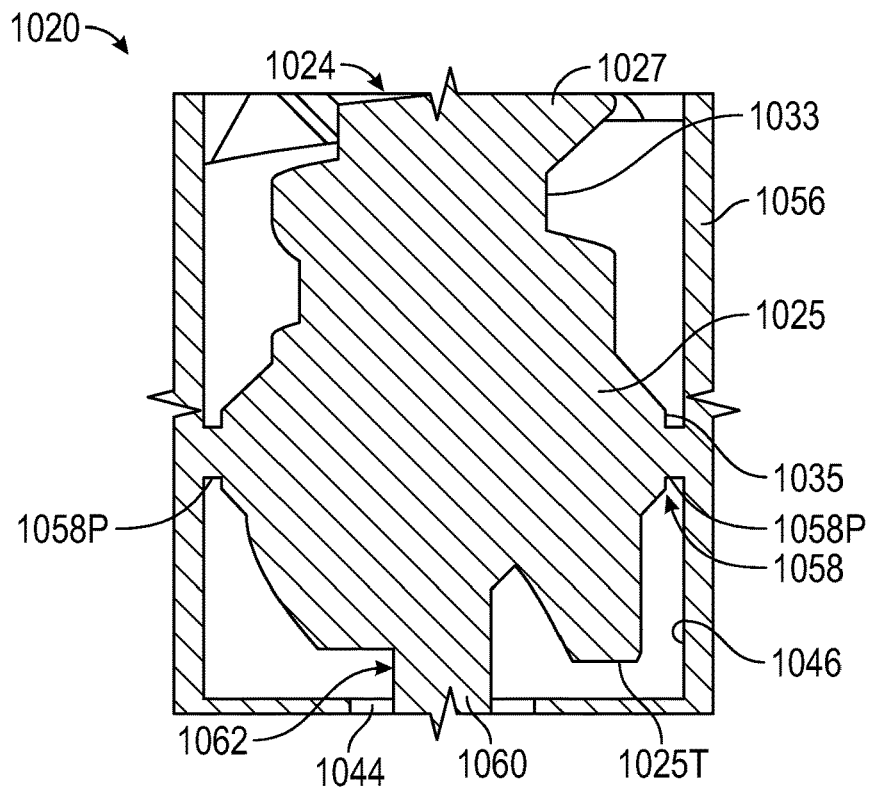
Figure 37:
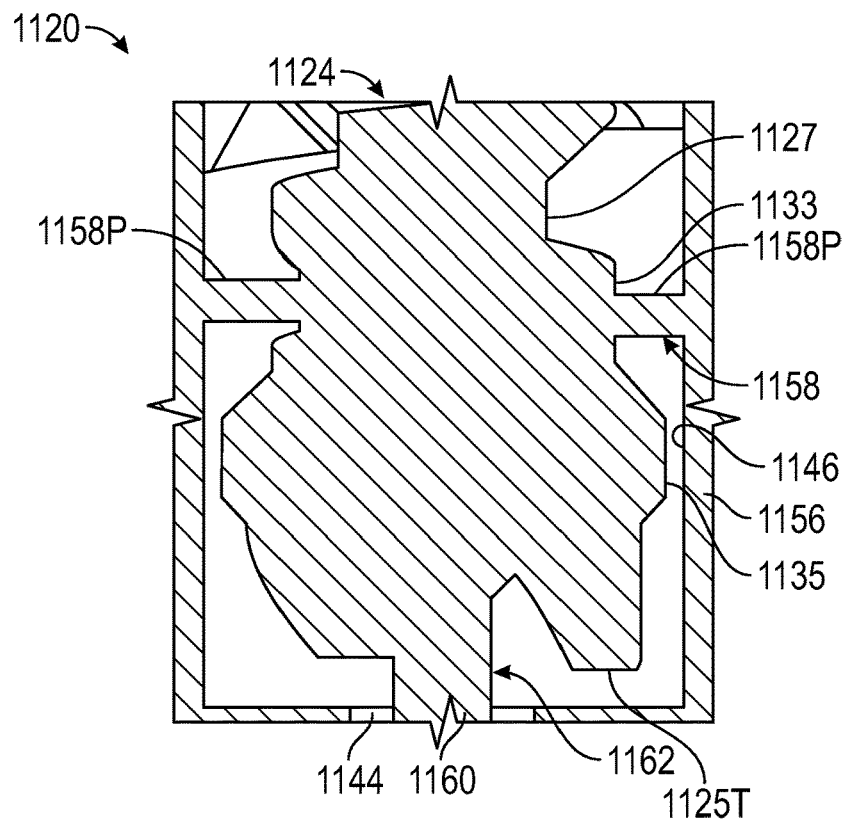

The first breakable connection and/or second breakable connection may be established along various positions of the respective fastener, including any of the positions disclosed herein, such as a top portion 425T of the shank portion 425 as illustrated by the first breakable connection 458 and second breakable connection 462 of FIG. 30. Establishing the first breakable connection 458 and second breakable connection 462 along the top portion 425T may reduce a complexity of forming the implant 420. The first breakable connection and/or second breakable connection may be established along other positions of the respective fastener, such as along a sidewall or circumference 1035 of the head portion 1025 as illustrated by the first breakable connection 1058 in FIG. 36 and/or along a circumference 1133 of the shank portion 1127 as illustrated by the first breakable connection 1158 in FIG. 37.

Referring to FIG. 30, with continuing reference to FIG. 24, a remainder of the implant 420 may be printed or otherwise formed at step 480F. Step 480F may include printing or otherwise forming a remainder of the main body 422 including the baseplate 428 and/or augment 430 at step 480G.

Step 480G may include printing or otherwise forming an anchoring stem 450 to establish the inner wall 456. The scaffold 440 may at least partially surround the anchoring stem 450. The anchoring stem 450 may be dimensioned to extend outwardly from the augment body 438 along the longitudinal axis X. Step 480G may include establishing an array of bone growth openings 454 in the anchoring stem 450 at a position outwardly from the rear face 441 of the augment 430. The bone growth openings 454 may be circumferentially distributed about a periphery 451 of a cage 452 or another portion of the anchoring stem 450. The bone growth openings 454 may interconnect the passage 446 and an external surface of the anchoring stem 450.

Step 480F may include printing or otherwise forming a remainder of the fastener 424 at step 480H. Step 480H may including printing or otherwise forming a reminder of the head portion 425 to a tip portion 431, a shank portion 427 extending from the head portion 425, and a plurality of threads 429 extending about a circumference 433 of the shank portion 427. Printing or otherwise forming the fastener 424 may occur such that the fastener 424 is cantilevered in the passage 446 from the first breakable connection 458 at the head portion 425 of the fastener 424, as illustrated in FIG. 30. The fastener 424 may be substantially solid or may include one or more passages 490 extending from the circumference 433 of the shank portion 427 (passages 490 shown in dashed lines for illustrative purposes). The passages 490 may extend through the fastener 424 to facilitate communication of blood, nutrients and other biological matter in the passage 446, which may improve healing.

The scaffold 440 may be printed or otherwise formed subsequent to, concurrently with, formation of the fastener 424 and tubular members 448. For example, the scaffold 440 may be printed around a periphery of the tubular members 448.

The method may include performing one or more finishing operations on the implant 420 at step 480I. Step 480I may include machining surfaces of the implant 420 according to a predetermined geometry. Step 480I may include applying one or more treatments to the implant 420, including applying surface coatings and treatments. Step 480I may include placing the implant 420 in sterile packaging for conveyance to the surgeon.

Figure 31:
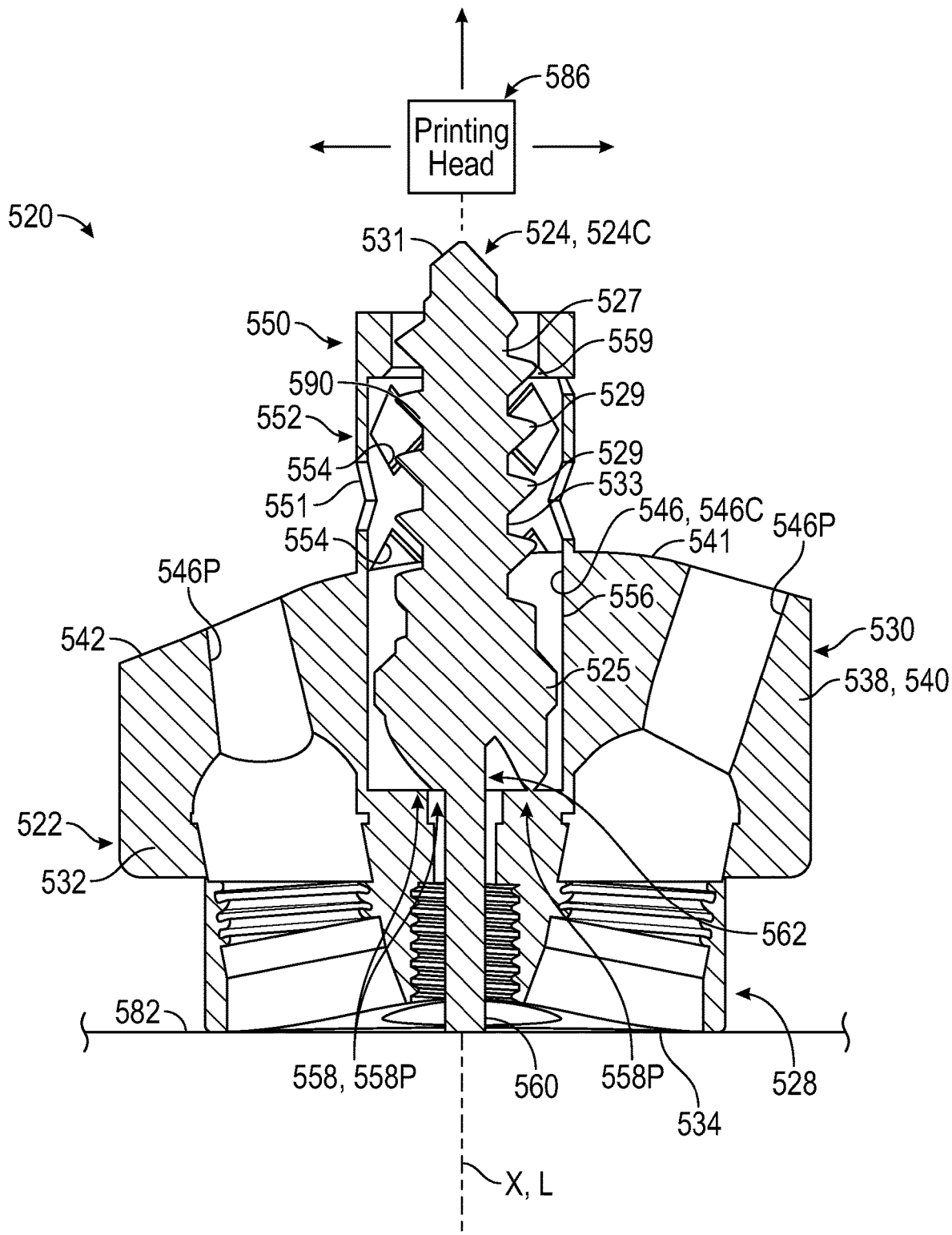
FIGS. 31-32 illustrate sectional view of other exemplary orthopaedic implants which may be associated with the method of FIG. 24.

In some implementations, the various steps of method 480 may be utilized such that the implant has a unitary construction, as illustrated by the implant 520 of FIG. 31. Steps 480A-480H may be performed such that substantially all portions of the implant 520 are printed or otherwise formed together to establish a monolithic or unitary component. For example, steps 480A-480H may be performed such that at least a baseplate portion 528, an augment portion 530 and at least one (or more) fastener 524 of the implant 520 are printed or integrally formed together to establish a monolithic or unitary component.

Figure 38:
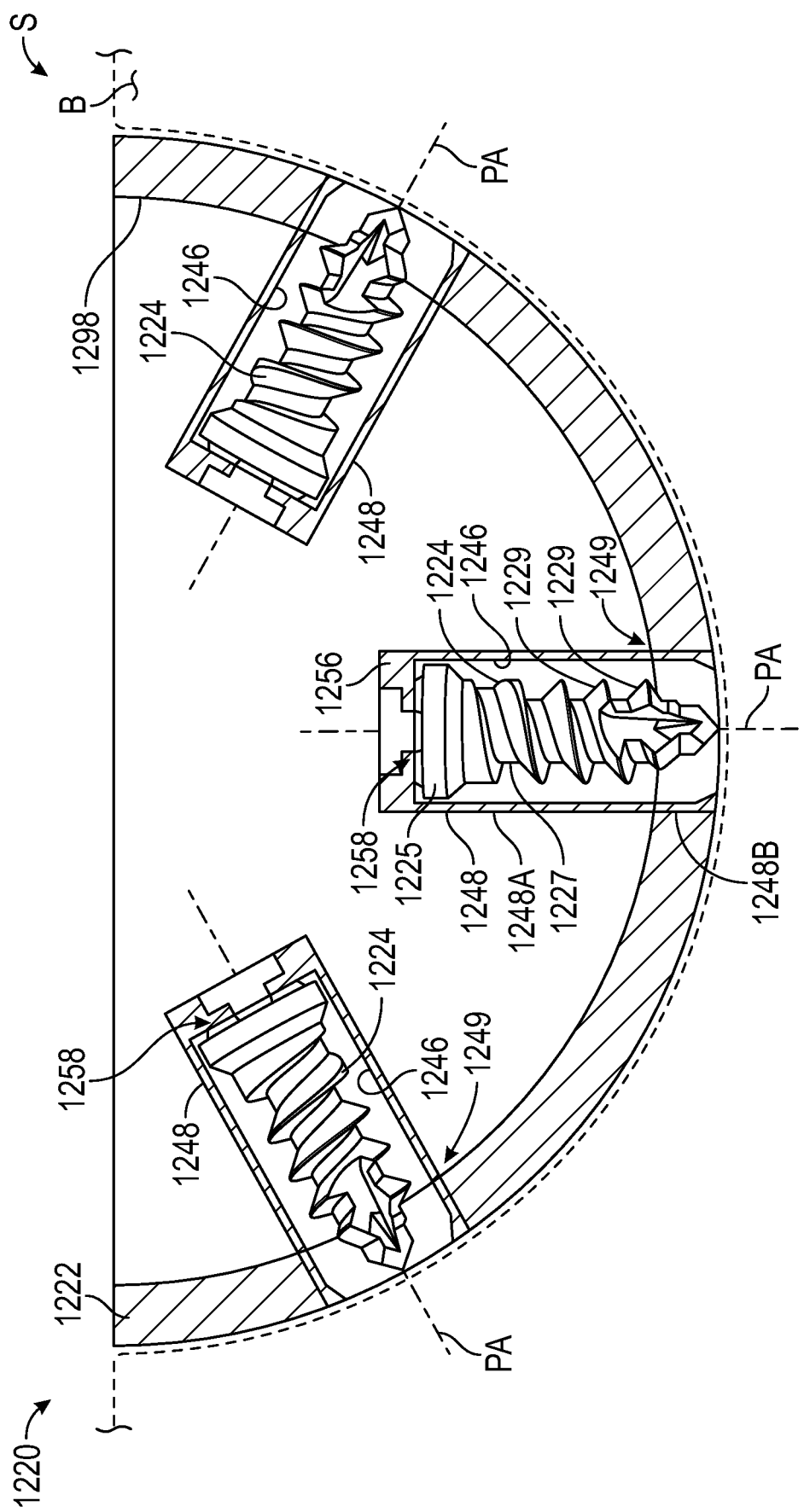
Figure 39:
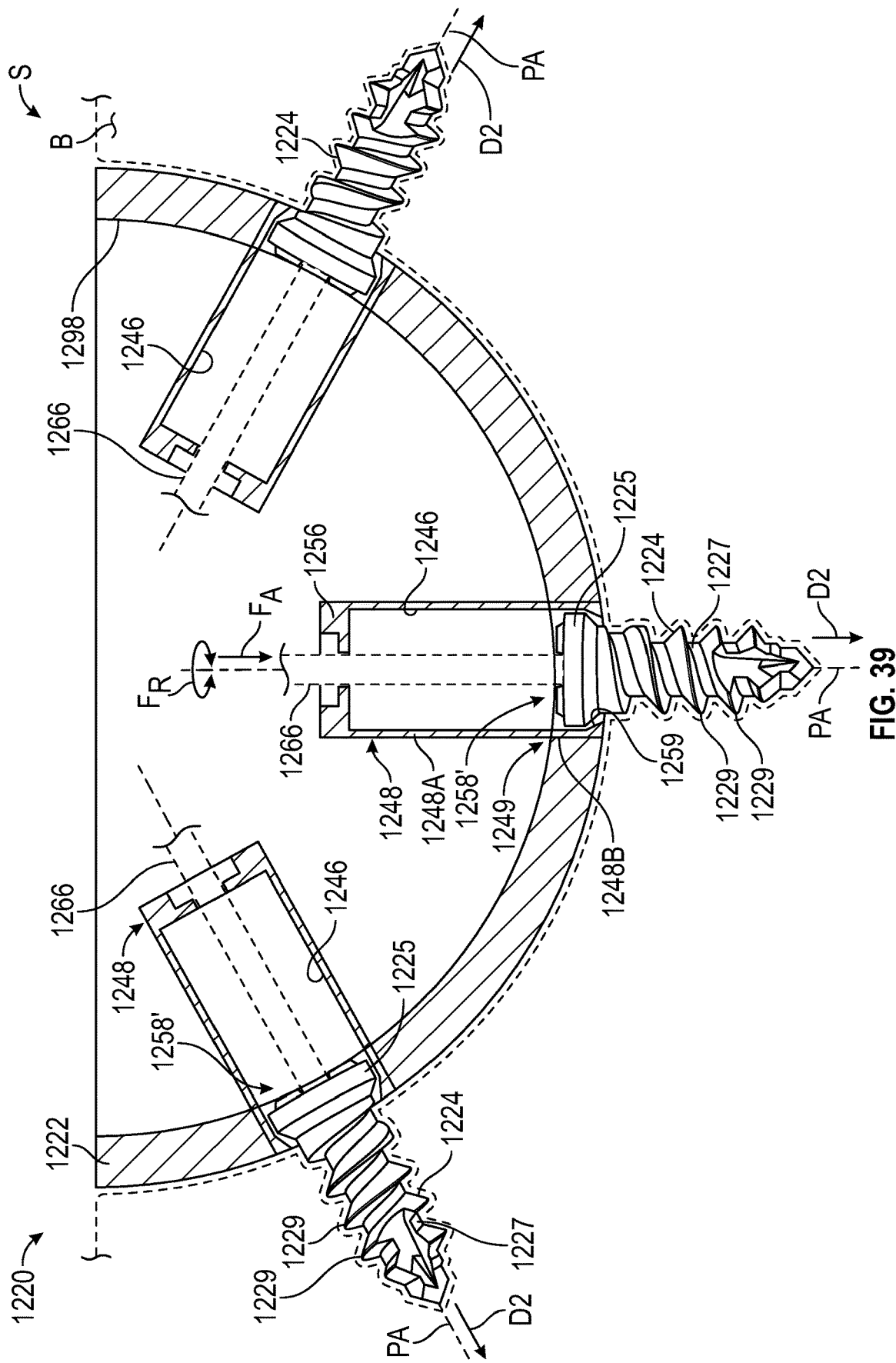
Figure 40:
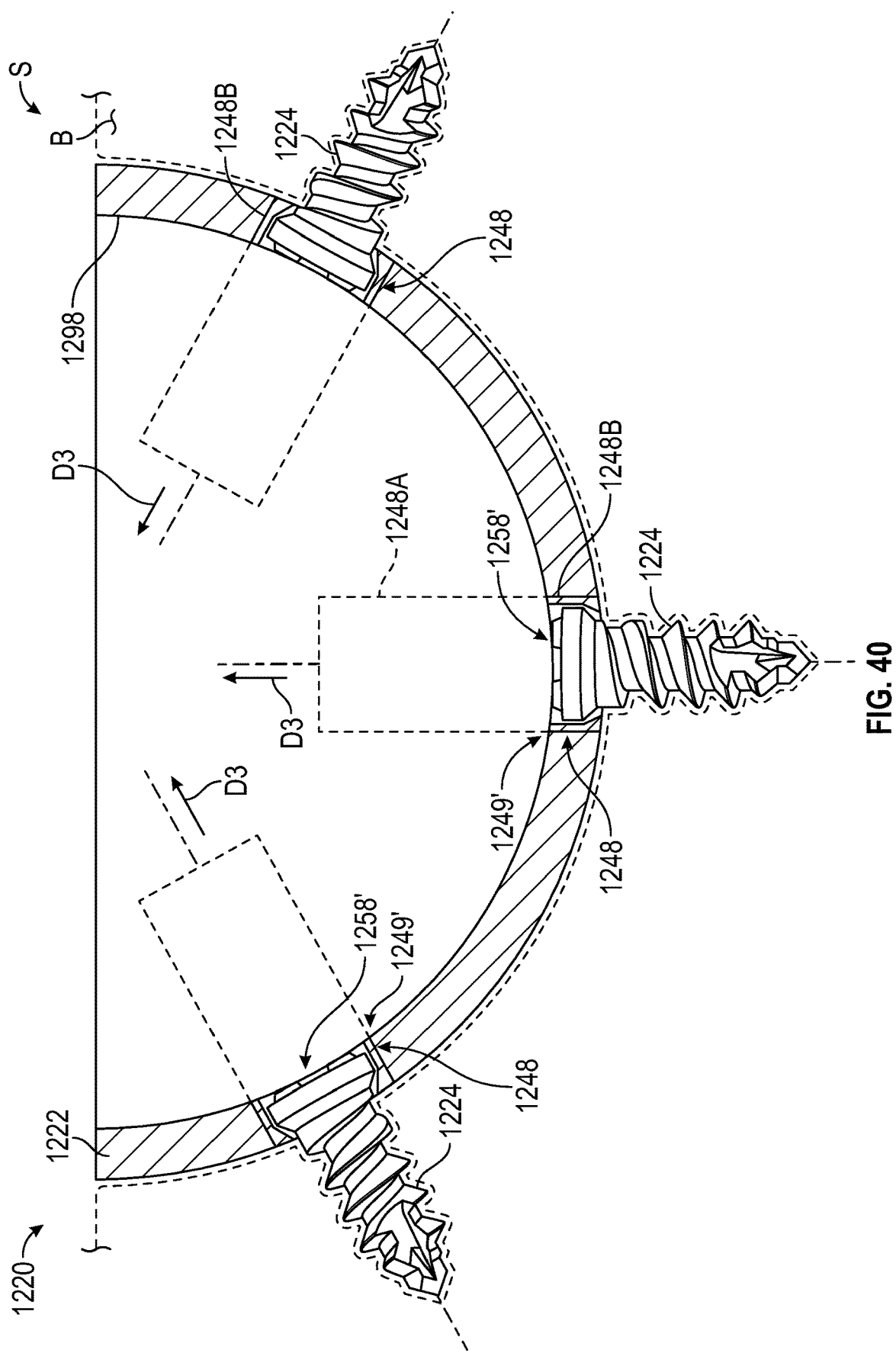
Figure 41:
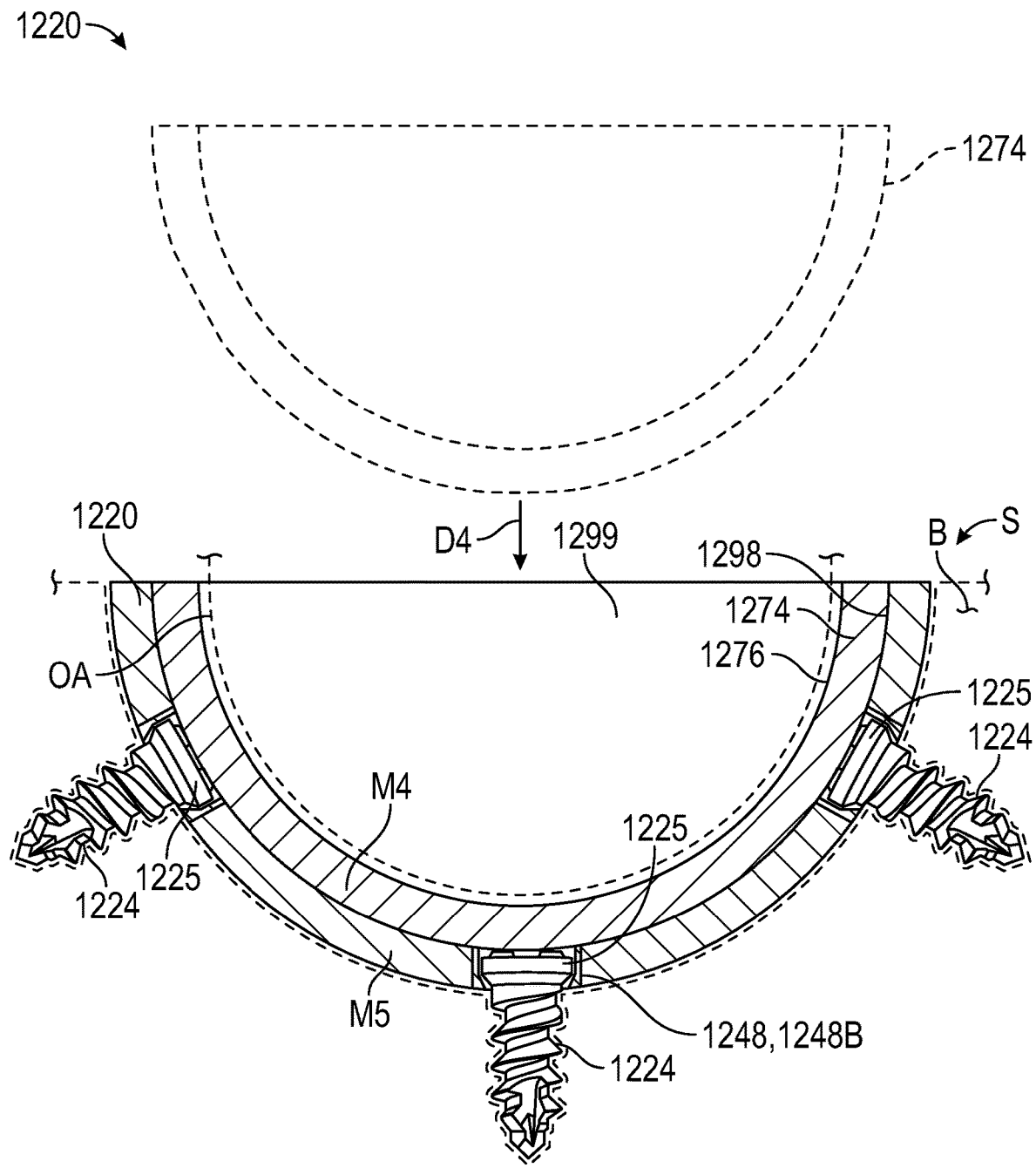
Figure 44:
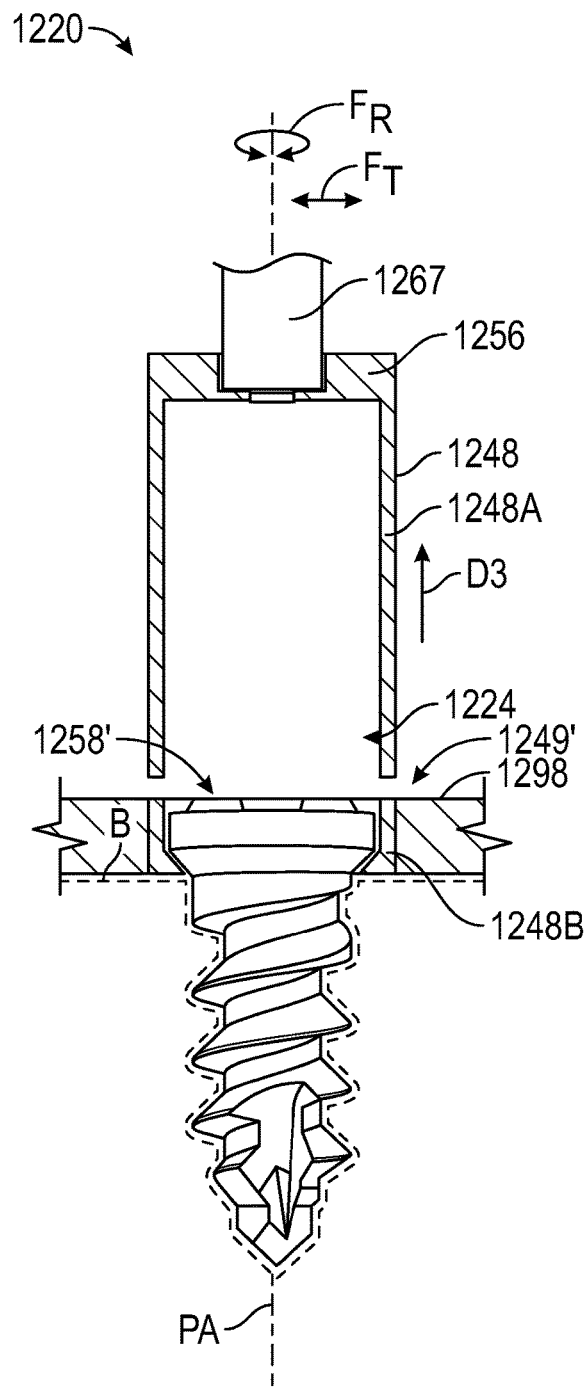
Figure 45:
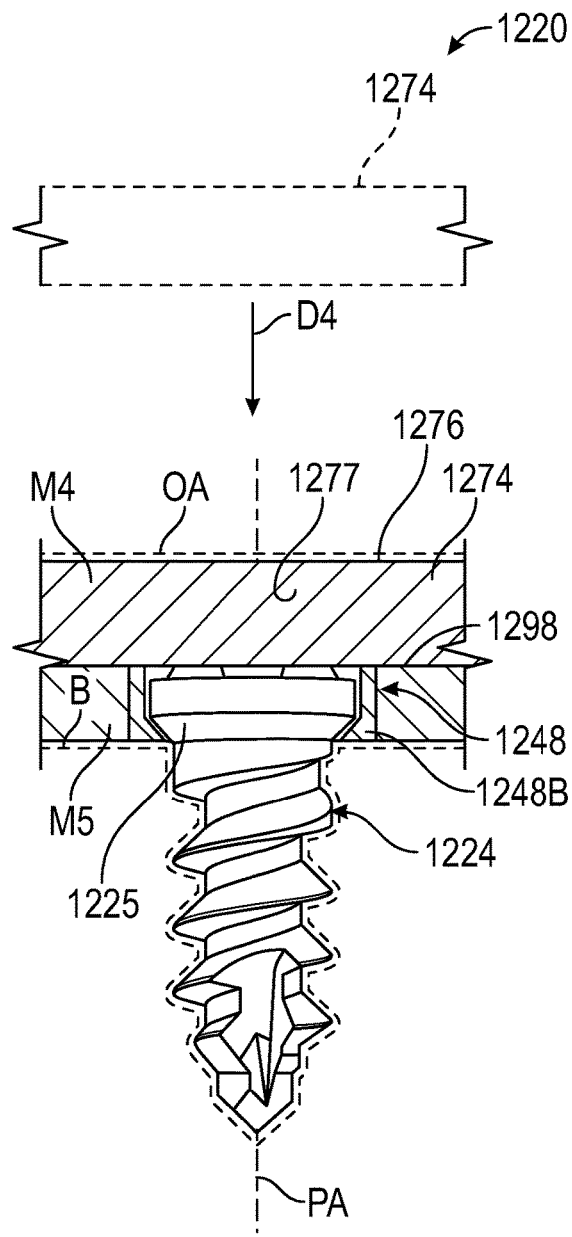

FIGS. 38-45 illustrate another exemplary orthopaedic implant 1220. The implant 1220 may incorporate any of the features of the implants disclosed herein, and may be formed utilizing any of the steps of method 480. FIGS. 38 and 42 illustrate the implant 1220 in a non-deployed state. FIGS. 39 and 43 illustrate the implant 1220 in a first deployed state. FIGS. 40 and 44 illustrate the implant 1220 in a second deployed state. FIGS. 41 and 45 illustrate the implant 1220 in a third deployed state.

Referring to FIG. 38, the implant 1220 may include a main body 1222 dimensioned to abut against bone B at a surgical site S (indicated in dashed lines for illustrative purposes). The bone B may be associated with a joint, including any of the joints disclosed herein. For example, the main body 1222 may establish an acetabular cup having a generally hemispherical geometry for restoring functionality to a hip joint. The main body 1222 of the implant 1220 may be securable to an acetabulum and may be dimensioned to cooperate with a femoral head at least partially received in a cavity 1299 (FIG. 41).

The implant 1220 may include one or more tubular members 1248 coupled to the main body 1222. The tubular members 1248 may have a generally tubular geometry or another geometry. The tubular members 1248 may be integrally formed with the main body 1222 or may be separate and distinct components mechanically attached or otherwise secured to the main body 1222. The tubular members 1248 may be dimensioned to be at least partially received in a recess 1298 established by the main body 1222.

Each tubular member 1248 may be dimensioned to establish a respective passage 1246. Each passage 1246 is dimensioned to at least partially or completely receive a respective fastener 1224 such that the tubular member 1248 serves as a carrier for the fastener 1224. The fastener 1224 may include any of the fasteners disclosed herein. The fastener 1224 may be a compression screw and may include a head portion 1225 and a shank portion 1227 extending from the head portion 1125. The shank portion 1227 may include one or more threads 1229. Each fastener 1224 may be dimensioned to extend along a respective passage axis PA.

Each fastener 1224 may be coupled to the tubular member 1248 at a first breakable connection 1258. The first breakable connection 1258 may include one or more separate and discreet breakable connection points 1258P distributed along surfaces of an inner wall 1256 of the implant 1220 and the fastener 1224, as illustrated in FIG. 42. The first breakable connection 1258 may be established by any of the breakable connections disclosed herein, such as a frangible connection including one or more connection points having a reduced thickness, scoring, perforations, and/or different material compositions (e.g., different densities), etc.

Each tubular member 1248 may include a first portion 1248A and a second portion 1248B extending from the first portion 1248A. The first portion 1248A and second portion 1248B may be integrally formed or may be separate and distinct components mechanically attached or otherwise secured to each other. In implementations, the first portion 1248A and second portion 1248B are coupled at a third breakable connection 1249. The third breakable connection 1249 may be established by any of the breakable connections disclosed herein, such as a frangible connection including one or more connection points having a reduced thickness, scoring, perforations, and/or different material compositions (e.g., different densities), etc.

The head portion 1225 of the fastener 1224 may be dimensioned to contact an abutment 1259 to limit axial movement of the fastener 1224 along the passage axis PA, as illustrated in FIG. 43. The second portion 1248B of the tubular member 1248 may be dimensioned to establish the abutment 1259.

Referring to FIG. 39, the first breakable connection 1258 may be dimensioned to be severed in response to a predetermined amount of force applied to the head portion 1225 or another portion of the fastener 1224. A driver 1266 may be utilized to engage the fastener 1224 and apply the predetermined amount of force, as illustrated in FIG. 43 (also shown in dashed lines in FIG. 39 for illustrative purposes). For example, the first breakable connection 1258 may be severed in response to the driver 1266 applying an axial force $F_A$ and/or rotational force $F_R$ to the head portion 1225 of the fastener 1224 relative to the passage axis PA, as illustrated by first breakable connection 1258' of FIG. 43.

The first breakable connection 1258 may be dimensioned to sever in response to a first predetermined quantity of torque applied to the fastener 1224, such as applying the force $F_R$ about the passage axis PA. The shank portion 1227 of each fastener 1224 may be moved in a direction D2 outwardly of the respective passage 1246 relative to the passage axis PA and into the bone B to secure the implant 1220 at the surgical site S, as illustrated by FIGS. 39 and 43.

Referring to FIG. 40, the third breakable connection 1249 may be severed in response to a predetermined amount of force applied to the first portion 1248A or another portion of the tubular member 1248 (first portion 1248A shown in dashed lines in FIG. 40 for illustrative purposes). Referring to FIG. 44, with continuing reference to FIG. 40, a driver 1267 may be utilized to engage the first portion 1248A or another portion of the tubular member 1248 and apply the predetermined amount of force. For example, the third breakable connection 1249 may be severed in response to the driver 1267 applying an axial force $F_A$, rotational force $F_R$ and/or transverse (e.g., radial) force $F_T$ to the first portion 1248A or another portion of the tubular member 1248 relative to the passage axis PA, as illustrated by the third breakable connection 1249'. The first portion 1248A may be moved in a direction D3 subsequent to being released from the second portion 1248B and removed from the recess 1298 (shown in dashed lines in FIG. 40 for illustrative purposes).

Referring to FIG. 41, the implant 1220 may include an articulation member 1274 mechanically attached or otherwise secured to the main body 1222. The articulation member 1274 may be moved in a direction D4 at least partially or completely into the recess 1298 to abut against the main body 1222, as illustrated in FIGS. 41 and 45. The articulation member 1274 may serve as a liner in an installed position, and the main body 1222 may serve as a shell. The articulation member 1274 may extend at least partially along the main body 1222. The articulation member 1274 may comprise a fourth material M4 that may be the same or may differ from a fifth material M5 of the main body 1222. The materials M4, M5 may include any of the materials disclosed herein, including metallic and/or non-metallic materials.

The articulation member 1274 may include an articulation surface 1276 dimensioned to mate with an opposed articular surface OA (shown in dashed lines for illustrative purposes). The articular surface OA may be associated with an adjacent bone at the surgical site S, such as a femoral head or another bone forming the respective joint. The articular surface OA may be established by a bone surface and/or an opposed implant. The articulation surface 1276 may have various geometries that complement a geometry of the opposed articular surface OA, such as a generally convex geometry or a generally concave geometry as illustrated in FIG. 41.

Various techniques may be utilized to secure the articulation member 1274 to the main body 1222, such as bonding together surfaces of the articulation member 1274 and main body 1222 and/or securing the components together utilizing one or more fasteners. The removable aspect of the first portion 1248A of each tubular member 1248 may serve to reduce a thickness of the articulation member 1274.

The novel implants and methods of this disclosure may provide versatility in securing the implants with fasteners to bone at a surgical site. The disclosed fasteners incorporated into the implants during formation may facilitate installation of the implant including more closely aligning the respective fastener to a pre-operative plan, which may reduce surgical duration and improve healing. Forming fasteners with the implants may also reduce separate sterile packaging and may reduce pre-operative planning and surgical duration. Reductions in surgical duration may be approximately 5-6 minutes or more. The disclosed driving members may serve as a torque limiter to reduce a likelihood that a surgeon over-torques the fastener and/or inserts the fastener too deeply, thereby increasing a likelihood of sufficient fixation.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure.

What is claimed is:

1. An orthopaedic implant comprising:
a main body including an internal wall establishing a passage, the passage extending inwardly from an external surface of the main body;
a fastener dimensioned to be partially received in bone, wherein the fastener is coupled to the internal wall at a first breakable connection along the passage, and a portion of the fastener is moveable outwardly from the passage in response to severing the first breakable connection;
wherein the fastener is a compression screw; and
wherein the compression screw includes a head portion and a shank portion extending from the head portion, threading extends about a circumference of the shank portion, and the fastener is cantilevered in the passage from the first breakable connection at the head portion.

2. The implant as recited in claim 1, wherein:
the main body includes a baseplate and an augment;
the baseplate includes a plate body extending along a longitudinal axis between a front face and a rear face; and
the augment includes an augment body dimensioned to contact bone, the augment body extending outwardly from the rear face of the baseplate to establish at least a portion of the passage.

3. The implant as recited in claim 2, wherein the augment body includes a porous scaffold extending between the external surface of the implant and the internal wall.

4. The implant as recited in claim 2, wherein the augment includes an anchoring stem, the passage extends through the anchoring stem, and the anchoring stem is dimensioned to extend outwardly from the augment body.

5. The implant as recited in claim 4, wherein the anchoring stem includes one or more bone growth openings circumferentially distributed about a periphery of the anchoring stem that interconnect the passage and an external surface of the anchoring stem.

6. The implant as recited in claim 2, wherein the plate body establishes a central aperture extending along the longitudinal axis between the front face and the passage.

7. The implant as recited in claim 6, wherein:
the plate body establishes a plurality of peripheral apertures circumferentially distributed about the central aperture relative to the longitudinal axis;
the augment establishes a plurality of peripheral passages at least partially aligned with respective ones of the peripheral apertures along a passage axis, and the peripheral passages extend between the rear face of the baseplate and the external surface of the implant; and
each respective pair of the peripheral apertures and the peripheral passages is dimensioned to at least partially receive a respective fastener along the passage axis, and each respective fastener is dimensioned to be at least partially received in bone.

8. The implant as recited in claim 2, further comprising:
an articulation member secured to the baseplate adjacent the front face, the articulation member including an articulating surface dimensioned to mate with an opposed articular surface associated with an adjacent bone.

9. The implant as recited in claim 1, wherein the first breakable connection includes a plurality of connection points extending between the fastener and the internal wall.

10. The implant as recited in claim 1, wherein the fastener establishes a passage dimensioned to at least partially receive a guide wire.

11. The implant as recited in claim 1, wherein the first breakable connection includes a plurality of breakable connection points interconnecting the internal wall and the head portion of the compression screw, and the breakable connection points are distributed about a longitudinal axis of the compression screw.

12. The implant as recited in claim 11, further comprising:
a driving member coupled to the fastener at a second breakable connection; and
wherein the driving member includes an interface dimensioned to engage a driver to cause the first breakable connection to sever.

13. The implant as recited in claim 12, wherein:
the first breakable connection is severable in response to a first predetermined quantity of torque at the interface; and
the second breakable connection is dimensioned to sever in response to a second predetermined quantity of torque at the interface, and the second predetermined quantity of torque is greater than the first predetermined quantity of torque.

14. The implant as recited in claim 12, wherein the second breakable connection at least partially extends along the passage.

15. The implant as recited in claim 12, wherein the driving member and the compression screw are axially aligned relative to a longitudinal axis of the compression screw.

16. The implant as recited in claim 1, wherein:
the passage extends along a passage axis, the internal wall includes an abutment along the passage, and the abutment is spaced apart from the first breakable connection relative to the passage axis; and
the head portion is dimensioned to contact the abutment to limit movement of the compression screw along the passage axis.

17. The implant as recited in claim 1, further comprising:
a driving member coupled to the fastener at a second breakable connection; and
wherein the driving member includes an interface dimensioned to engage a driver to cause the first breakable connection to sever in response to a first predetermined quantity of torque at the interface.

18. The implant as recited in claim 17, wherein the second breakable connection is dimensioned to sever in response to a second predetermined quantity of torque at the interface, and the second predetermined quantity of torque is greater than the first predetermined quantity of torque.

19. An orthopaedic implant comprising:
   a main body including an internal wall establishing a passage, the passage extending inwardly from an external surface of the main body;
   a fastener dimensioned to be partially received in bone, wherein the fastener is coupled to the internal wall at a first breakable connection along the passage, and a portion of the fastener is moveable outwardly from the passage in response to severing the first breakable connection;
   a driving member coupled to the fastener at a second breakable connection;
   wherein the driving member includes an interface dimensioned to engage a driver to cause the first breakable connection to sever in response to a first predetermined quantity of torque at the interface; and
   wherein the second breakable connection is dimensioned to sever in response to a second predetermined quantity of torque at the interface, wherein the second predetermined quantity of torque is greater than the first predetermined quantity of torque.

20. The implant as recited in claim 19, wherein the second breakable connection at least partially extends along the passage.

21. A method of installing an orthopaedic implant at a surgical site comprising:
   positioning an implant along a bone at a surgical site, wherein the implant includes a main body including an internal wall establishing a passage and a fastener coupled to the internal wall of the main body at a first breakable connection along the passage, and the passage extends inwardly from an external surface of the main body;
   engaging an interface of the implant with a driver;
   severing the first breakable connection in response to moving the driver at the interface, and then moving the driver to cause the fastener to move at least partially outwardly from the passage and into the bone to secure the implant at the surgical site;
   wherein the fastener is a compression screw; and
   wherein the compression screw includes a head portion and a shank portion extending from the head portion, threading extends about a circumference of the shank portion, and the fastener is cantilevered in the passage from the first breakable connection at the head portion.

22. The method as recited in claim 21, wherein the step of severing the first breakable connection generates an audible click and/or tactile force.

23. The method as recited in claim 21, wherein:
   the implant includes a driving member coupled to the fastener at a second breakable connection, the driving member establishing the interface; and
   the step of severing the first breakable connection includes causing the driver to apply a first torque at the interface that exceeds a first predetermined quantity of torque.

24. The method as recited in claim 23, further comprising:
   severing the second breakable connection subsequent to the step of severing the first breakable connection in response to causing the driver to apply a second torque at the interface that exceeds a second predetermined quantity of torque.

25. The method as recited in claim 21, wherein the main body includes an anchoring stem, the passage extends through the anchoring stem, a portion of the anchoring stem establishes a plurality of bone growth openings circumferentially distributed about a periphery of the anchoring stem that interconnect the passage and an external surface of the anchoring stem, and further comprising:
   forming a recess in the bone; and
   positioning the portion of the anchoring stem in the recess.

26. The method as recited in claim 21, wherein the passage extends along a longitudinal axis, the main body establishes a plurality of peripheral apertures circumferentially distributed about the longitudinal axis, and further comprising:
   positioning a plurality of fasteners at least partially in respective ones of the peripheral apertures and then at least partially into the bone to secure the implant at the surgical site.

27. The method as recited in claim 21, further comprising:
   securing an articulation member to a front face of the main body, the articulation member including an articulating surface dimensioned to mate with an opposed articular member associated with an adjacent bone at the surgical site.

* * * * *